(12) United States Patent
McNeish et al.

(10) Patent No.: US 6,693,226 B1
(45) Date of Patent: Feb. 17, 2004

(54) TRANSGENIC MICE EXPRESSING HUMAN P25

(75) Inventors: John D. McNeish, Mystic, CT (US); Michael K. Ahlijanian, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/496,445

(22) Filed: Feb. 2, 2000

Related U.S. Application Data

(60) Provisional application No. 60/118,478, filed on Feb. 3, 1999.

(51) Int. Cl.$^7$ ............... A01K 67/00; A01K 67/027; A01K 67/033; G01N 33/00
(52) U.S. Cl. .................. 800/18; 800/3; 800/12
(58) Field of Search ................ 800/3, 12, 13, 800/14, 18; 536/24.1, 23.1

(56) References Cited

PUBLICATIONS

Niemann, Transgenic farm animals get off the ground, Transgenic Research 7, 73–75, 1998.*
Sigmund, Viewpoint: Are Studies in Genetically Altered Mice Out of Control?, Arterioscler Thromb Vasc. Biol. Jun. 2000, pp. 1425–1429.*
Cameron, Recent Advances in Transgenic Technology, Molecular Biotechnology, vol. 7, 1997, pp 253–265.*
Wang et al., Formation of B–Amyloid protein deposits in brains of transgenic mice, Nature, vol. 352, Jul. 18,1991, pp. 239–244.*
Higgins et al., Transgenic Mice Expressing Human B–APP751, But Not Mice Expressing B–App695, Display Early Alzheimer's Disease–like Histopathology, Annals New York Academy of Sciences, pp 224–227.*
Lew et al., A brain–specific activator of cyclin–dependent kinase 5, Nature vol. 371, Sep. 29, 1994, pp. 423–426.*
Baumann et al., Abnormal Alzheimer–like, phosphorylation of tau–protein by cyclin–dependent kinases cdk2 and cdk5, Febs 13455, vol. 336, No. 3, 417–424, Dec. 1993.*
Kim et al., HBx gene of hepatitis B virus induces liver cancer in transgenic mice, Letters of Nature, vol. 351, May 23, 1991, pp 317–320.*
Benn et al., Hepaptits B virus HBx protein deregulates cell cycle checkpoint controls, Proc. Natl., Acad., Sci, USA, vol. 92, pp 11215–11219, Nov. 1995, Biochemistry.*

* cited by examiner

Primary Examiner—Deborah Crouch
(74) Attorney, Agent, or Firm—Peter C. Richardson; Paul H. Ginsburg; E. Victor Donahue

(57) ABSTRACT

The invention provides transgenic, non-human animals and transgenic non-human mammalian cells harboring a transgene encoding a p25 (activator of the protein kinase cdk 5) polypeptide. The two neuropathological lesions associated with Alzheimer's disease (AD) are amyloid plaques and neurofibrillary tangles (NFTs), composed predominantly of amyloid β peptides and hyperphosphorylated tau, respectvely. While animal models for plaque formation exist, there is no animal model that recapitulates the formation of NFTs. This invention provides transgenic mice that overexpress human p25, an activator of cdk5, resulting in tau that is hyperphosphorylated at AD-relevant epitopes. Deposition of tau is detected in the amygdala, thalamus and cortex. Increased phosphorylated neurofilament, silver-positive neurons and neuronal death are also observed in these regions. We conclude that the overexpression of p25, an activator of cdk5, is sufficient to produce hyperphosphorylation of tau and neuronal death. The p25 transgenic mouse represents the first model for tau pathology in AD.

3 Claims, 14 Drawing Sheets

TRANSGENIC MICE EXPRESSING HUMAN P25

This application claims benefit of priority to provisional application No. 60/118,478, filed Feb. 3, 1999.

TECHNICAL FIELD

The invention provides transgenic, non-human animals and transgenic non-human mammalian cells harboring a transgene encoding a p25 polypeptide, an activator of the protein kinase cdk5. The invention also provides non-human animals and cells comprising a transgene encoding a p25 polypeptide and further comprising functional overexpression of p25, the p25 transgene and targeting constructs used to produce such transgenic cells and animals, transgenes encoding human p25 polypeptide sequences and methods for using the transgenic animals in pharmaceutical screening and as commercial research animals for modeling neurodegenerative disease such as Alzheimer's disease and p25/cdk5 biochemistry in vivo.

BACKGROUND OF THE INVENTION

Throughout the specification, a number of publications are cited. These publications are incorporated by reference in their entirety. A complete listing of the publications appears later in the specification.

Alzheimer's disease (AD) is a progressive, neurodegenerative disorder characterized by loss of cognitive function. The primary neuropathological lesions in AD are amyloid plaques and neurofibrillary tangles (NFTs). Amyloid plaques are composed primarily of amyloid beta (Ab) peptides, varying in length from 39–42 amino acids, which are derived from amyloid precursor protein (APP) (reviewed in 1). NFTs are composed of the microtubule binding protein tau that is hyperphosphorylated at epitopes which exist in a predominantly unphosphorylated state in disease-free brain (2–4). The respective roles that these lesions play in the neuronal loss and dementia observed in patients with AD remain controversial.

The precise mechanism of NFT formation is not clear but work from many laboratories suggests that hyperphosphorylation of tau may be an important event. The paired helical filament (PHF) is the fundamental unit of the NFT. Hyperphosporylation of tau at serine or threonine residues followed by proline (SP or TP), epitopes which are concentrated at the amino and carboxy termini of tau, results in loss of affinity for microtubules, and a presumed concomittant increase in the concentration of cytoplasmic tau (5–8). However, phosphorylation of tau at serine 262, which is not followed by proline, can also reduce the affinity of tau for microtubules (9). In vitro experiments with purified tau show that in the presence of endogenous cations (e.g., mRNA, heparin sulfate proteoglycan), tau polymerizes to form structures indistinguishable from the PHF seen in AD brain (10,11). The cation-dependent formation of PHF in vitro is independent of the phosphorylation state of tau, suggesting that the key permissive event in initiating PHF formation may be an increase in the cytoplasmic concentration of tau. In support of this hypothesis, recent evidence (12–14) indicates that the mutations in the tau gene associated with susceptibility to a form of inherited dementia called frontotemporal dementia and Parkinsonism linked to chromosome 17 (FTDP-17), reduce the affinity of tau for microtubules (15). Therefore these mutations, like hyperphosphorylation, may result in an increase in cytoplasmic tau concentrations. In the presence of endogenous cations, this increase is presumed to permit PHF formation followed by NFT assembly and, ultimately, neuronal death.

As with other phosphoproteins, the phosphorylation state of tau is the sum of protein kinase and protein phosphatase activity. Thus hyperphosphorylation of tau in AD may be due to an increase in kinase activity or a decrease in phosphatase activity. While many protein kinases phosphorylate tau at AD-relevant epitopes in vitro (reviewed in 16,17), only two have been co-purified with microtubules from mammalian brain, GSK3b and cdk5 (18). To our knowledge, only these two kinases will phosphorylate tau when transfected heterologously into mammalian cells (19, 24). We chose to focus on cdk5 vs. GSK3b as the latter plays a role in energy metabolism and is expressed in an active form in all cells, while cdk5 is only active in neurons (vide infra).

The kinase cdk5 is a member of the cyclin-dependent protein kinase family and is expressed in nearly all cells (reviewed in 25,26). Unlike other members of the cdk family, there is no known cyclin which activates cdk5. Rather, the positive allosteric regulators of cdk5 are p35 (27), amino terminal proteolytic fragments of p35, e.g, p25, p23 or p21 (28,29) and p39 (30). These proteins share minimal amino acid sequence homology to cyclins (27–29) but computer modeling and biochemical experiments suggests that the mechanism of activation of cdk5 by p25/35 may be similar to that of cyclin A activation of cdk2 (31–33). The protein p25/35 is expressed predominantly in neurons implying that most cdk5 activity is concentrated in neuronal structures (27,28). The protein p35 has a relatively short half life within cells and is rapidly ubiquitinated, suggesting tight regulation of cdk5 activity in neurons (34). The kinase cdk5 plays a pivotal role in neuronal development as evidenced by the abnormal corticogenesis and perinatal lethality of cdk5 knockout mice (35) and the disturbances in neuronal migration and early death in p35 knock-out mice (36). In developmental studies in rodents, the peak catalytic activity of cdk5 occurs at E11 or 12, lending further support for the role of cdk5 in neurogenesis (37,38). Furthermore, in primary cultured neurons, cdk5/p35 is localized to growth cones suggesting a role in neurite outgrowth (39). Recently, evidence of signaling pathways which may modulate cdk5 activity have emerged. For example, it has been demonstrated that cdk5/p35 interacts with Rac and modulates PAK activity (40), and that laminin-enhanced outgrowth of cerebellar neurons is disrupted by suppression of p35 expression (41). A few substrates for cdk5 have been identified and are consistent with the presumed role in neurite outgrowth and plasma membrane dynamics. These include cytoskeletal proteins such as tau (42–45) and neurofilament (46–48), synaptic vesicle proteins such as synapsin and Munc-18 (49,50) and the retinoblastoma protein (51). Nevertheless, neither a clear picture of a signal transduction pathway(s) which regulates cdk5/p35 activity nor the role of both cdk5/p35 in mature brain have been elucidated.

A clear picture of the protein kinases responsible for the hyperphosphorylation of tau in AD is also lacking. However, evidence that cdk5 may a play a pathological role is accumulating. For example, in in vitro studies, cdk5 will phosphorylate up to eight different epitopes of tau, including those associated with AD and known to decrease the affinity of tau for microtubules (42–45). Additionally, heterologous co-transfection of cdk5/p25 with tau into mammalian cells also results in phosphorylation of several of these epitopes (24). Finally, immunohistochemical evidence suggests that cdk5 is proximal to NFTs in AD brain (52,53).

The development of experimental models of Alzheimer's disease that can be used to define further the underlying biochemical events involved in AD pathogenesis would be highly desirable. Such models could be employed, in one application, to screen for agents that alter the degenerative course of AD. For example, a model system of AD could be used to screen for environmental factors that induce or accelerate the pathogenesis of AD. Alternatively, an experimental model could be used to screen for agents that inhibit, prevent, or reverse the progression of AD. Such models could be employed to develop pharmaceuticals that are effective in preventing, arresting or reversing AD. Only humans and aged non-human primates develop any of the pathological features of AD. The expense and difficulty of using primates and the length of time required for developing the AD pathology makes extensive research on such animals prohibitive. Rodents do not develop AD, even at an extreme age. Despite various reports that certain treatments result in hyperphosphorylation of tau and/or neuronal death associated with the phosphorylation of tau, there is a need in the art for transgenic non-human animals which can produce hyperphosphorylation of tau and associated neuronal death.

Based on the above, it is clear that a need exists for nonhuman cells and nonhuman animals which produce hyperphosphorylation of tau and neuronal cell death. Thus, it is an object of the invention herein to provide methods and compositions for transferring transgenes and homologous recombination constructs into mammalian cells, especially into embryonic stem cells. It is also an object of the invention to provide transgenic non-human cells and transgenic nonhuman animals harboring transgenes resulting in the increased expression of p25, an activator of cdk5. Of further interest to the present invention are the application of such transgenic animals as in vivo systems for screening test compounds for the ability to inhibit or prevent the production of hyperphosphorylated tau and associated neuronal death. It is desirable to provide methods and systems for screening test compounds for the ability to inhibit or prevent the phosphorylation of tau and associated neuronal death. In particular, it is be desirable to base such methods and systems on inhibition of cdk5/p25, where the test compound blocks phosphorylation of tau mediated by cdk5/p25, the test compound also blocks neuronal death. Such methods and transgenic animals should provide a rapid, economical and suitable way for screening large numbers of test compounds.

We overexpressed human p25 in the brains of mice to determine if an increase in cdk5 activity would result in the hyperphosphorylation of tau at AD-relevant epitopes, and if this hyperphosphorylation would lead to neuronal death. In the brains of p25 transgenic mice, both tau and neurofilament are hyperphosphorylated, and many silver-positive neurons with tangle-like inclusions are present. The silver-positive neurons suggest ongoing neuronal death. These results demonstrate that overexpression of an activator of cdk5 is sufficient to produce tau and neurofilament phosphorylation and silver-positive neurons which are very similar to those seen in AD. The p25 transgenic mouse may serve as a model for the neurofibrillary pathology and neuronal death seen in AD.

SUMMARY OF THE INVENTION

In one embodiment, the present invention is directed to recombinant DNA comprising a rat neuron specific enolase promoter operably linked to a p25 encoding sequence of the human cdk5 gene encoding sequence.

In a preferred embodiment, the present invention is directed to recombinant DNA wherein said sequence encoding said p25 fragment is genomic DNA.

In another preferred embodiment, the present invention is directed to recombinant DNA wherein said sequence encoding said p25 fragment is cDNA.

In still another preferred embodiment, the present invention is directed to recombinant DNA wherein said sequence is that of SEQ ID NO: 4.

In yet another embodiment, the present invention is directed to a vector comprising recombinant DNA according to the present invention.

In another embodiment, the present invention is directed to eukaryotic cell lines comprising recombinant DNA according to the present invention.

In another embodiment, the present invention is directed to a transgenic non-human animal, or progeny thereof, whose germ cells and somatic cells express recombinant DNA according to the present invention.

In a preferred embodiment, the present invention is directed to a transgenic non-human animal, or progeny thereof, which is a mouse.

In a further embodiment, the present invention is directed to a method for treating an animal having a disease characterized by the expression of a p25 fragment of a human cdK5 gene comprising administering a therapeutically effective amount of an inhibitor of said p25 fragment.

In another embodiment, the present invention is directed to a method for determining the ability of a compound to inhibit the expression of a p25 fragment of a human cdk5 gene comprising the steps of:
a. creating a transgenic non-human animal by stably incorporating into the embryonic stem cells of said animal the recombinant DNA of claim 1;
b. growing said embryonic stem cells into a mature transgenic non human animal;
c. administering to said transgenic non-human animal the compound of interest;
d. measuring the inhibition of said p25 fragment by said compound.

In still another embodiment, the present invention is directed to a method for generating data to determining the ability of a compound to inhibit the expression of a p25 fragment of a human cdk5 gene comprising the steps of:
a. creating a transgenic non-human animal by stably incorporating into the embryonic stem cells of said animal the recombinant DNA of claim 1;
b. growing said embryonic stem cells into a mature transgenic non human animal;
c. administering to said transgenic non-human animal the compound of interest;
d. measuring the inhibition of said p25 fragment by said compound.
e. using the data derived from said inhibition to synthesize compounds capable of inhibiting said p25 fragment.

Expression of the transgene, p25, is apparent in the transgenic but not wild type mice.

Figure 2:
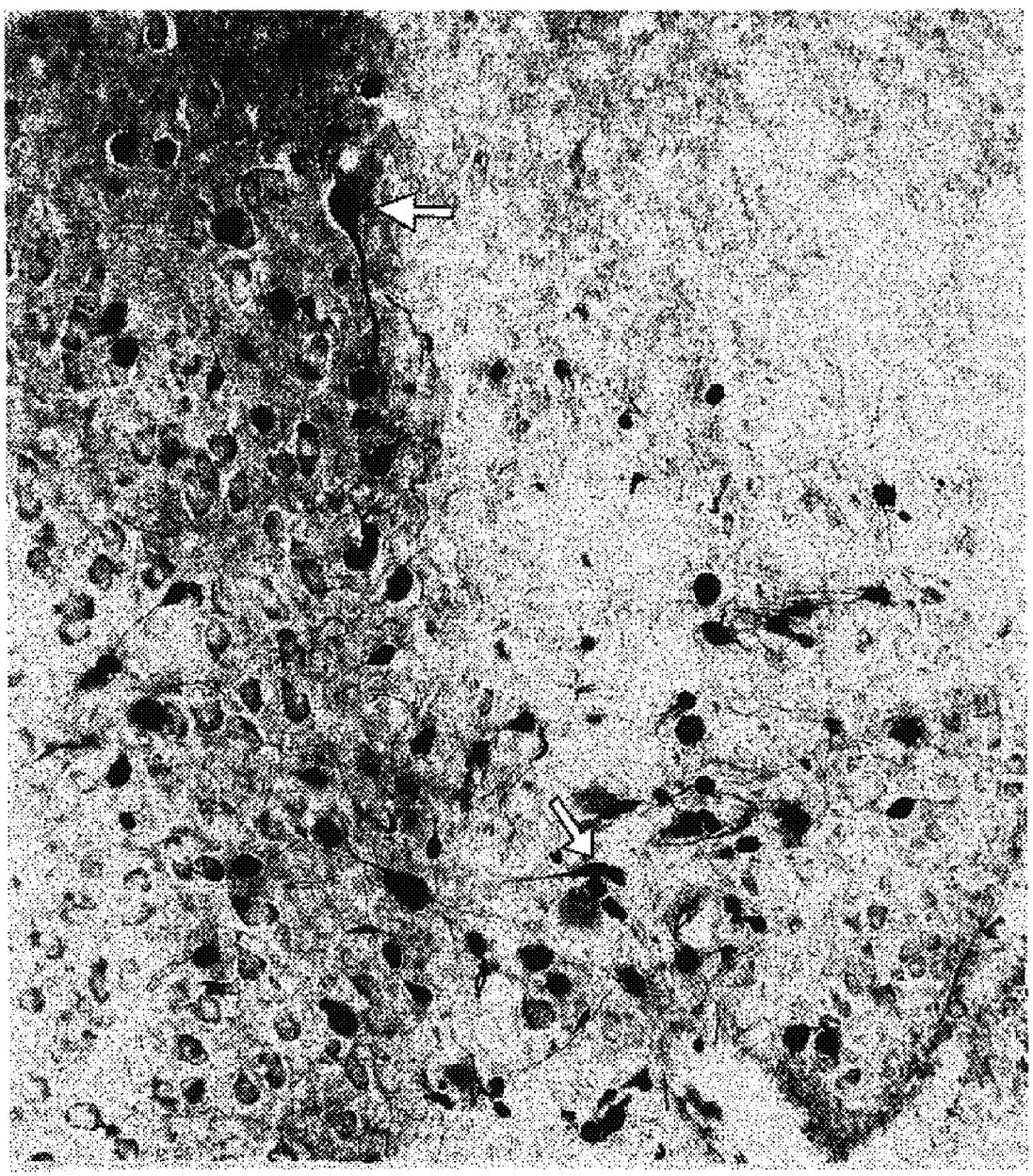

FIG. 2 displays a four month old transgenic mouse brain immunopositive for AT-8 (a commercially available antibody which specifically recognizes phopho-serine 202/205 of tau) specific in the rostral portion of the amygdala. Neuronal cell bodies with accompanying axons (arrows) are positive. Several dark-brown positive cells are seen in this field.

Figure 3:
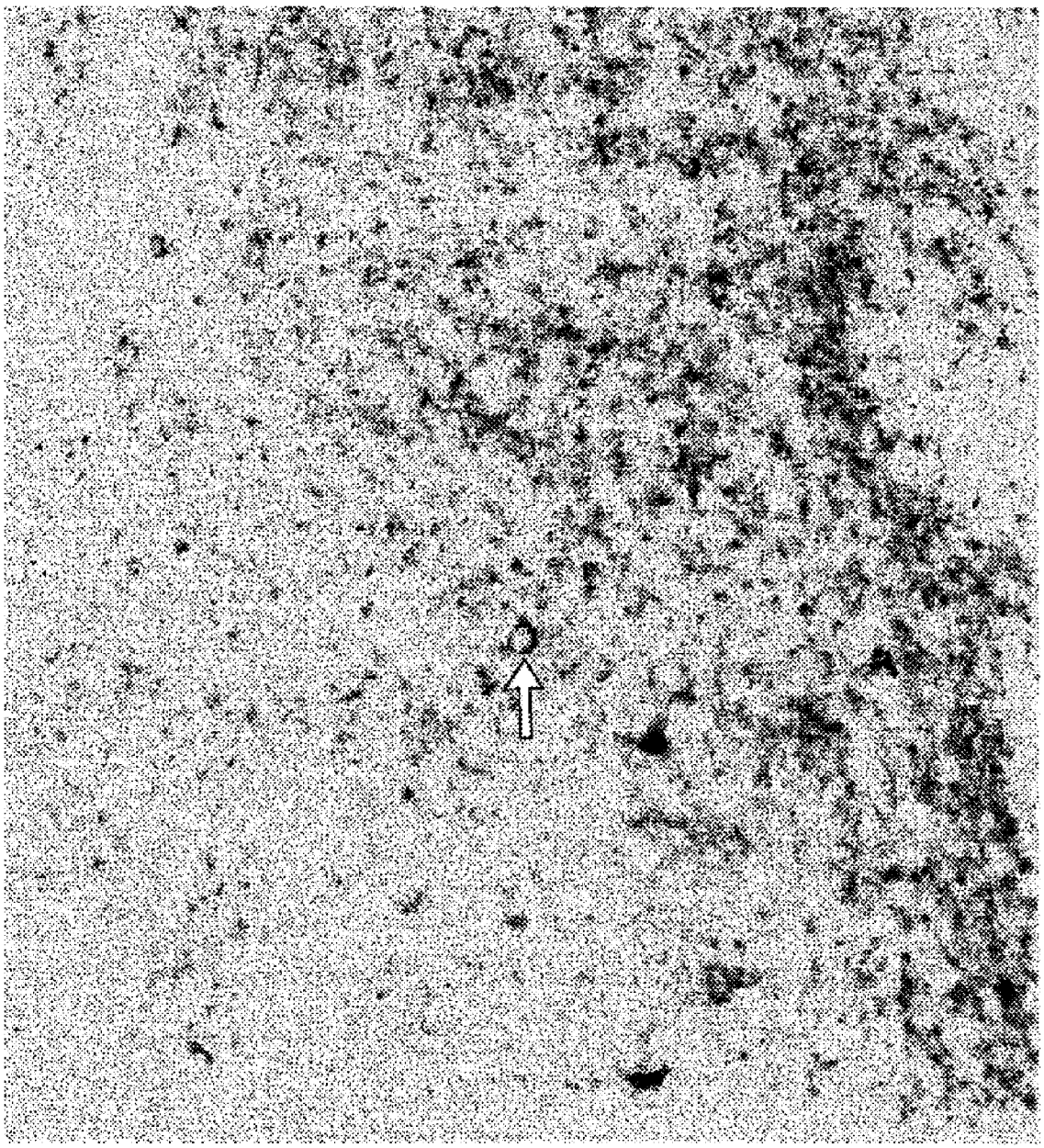

FIG. 3 shows a four month old wild-type mouse brain minimally positive for AT-8 in the rostral portion of the amygdala. A cell body exhibits non-specific positivity (arrow) due to the secondary antibody.

Figure 4:
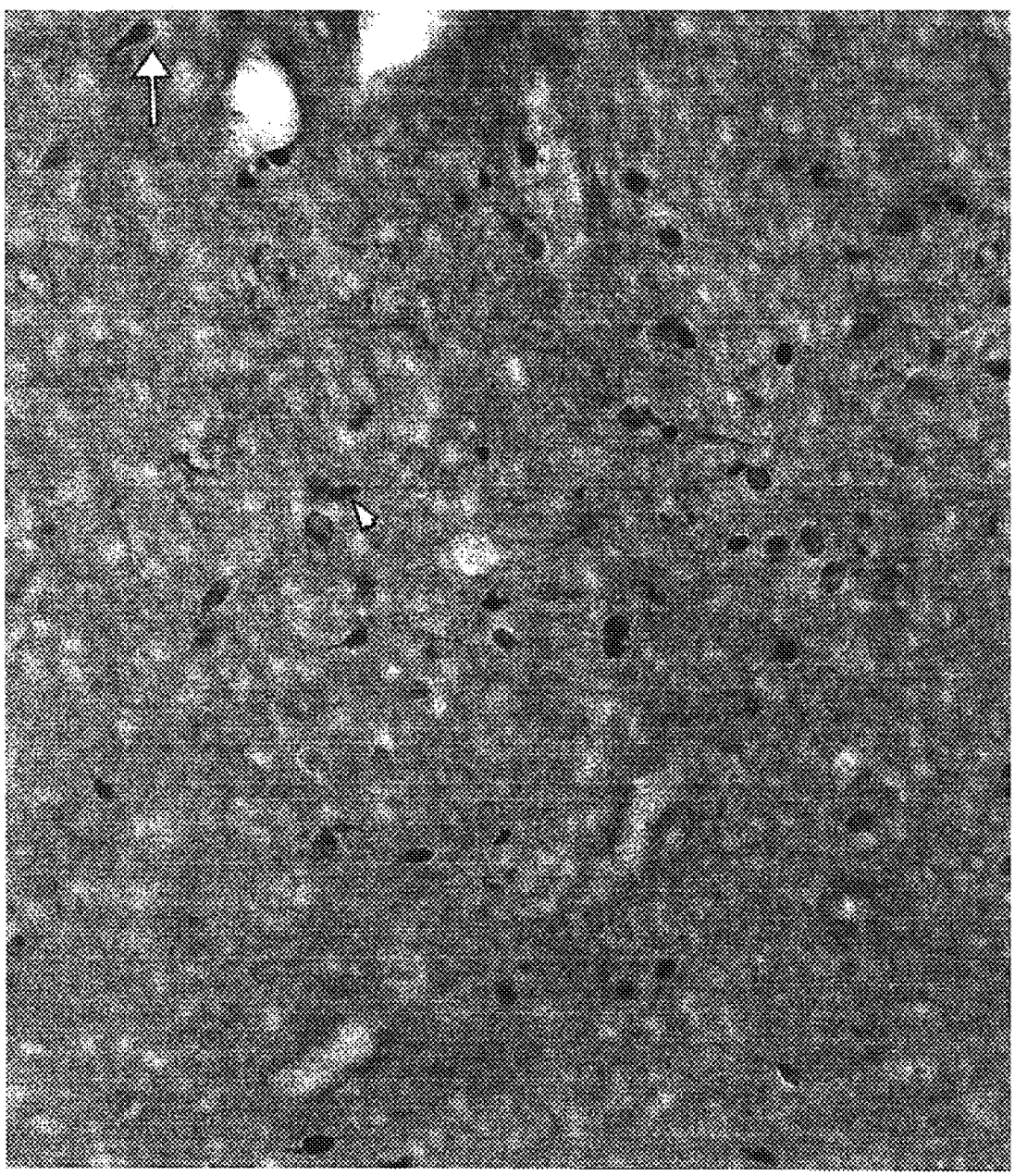

FIG. 4 shows a four month old transgenic mouse brain demonstrating PHF-13 (an antibody which recognizes phospho-serine 396/404 of tau; (gift from Dr. V. Lee, U. of Pennsylvania) immunopositivity in the rostral portion of the amygdala. Neuronal cell body with a thickened axon (arrow) is positive. Positive neuronal cell body (arrow head) with possible swollen/atrophied axon.

Figure 5:
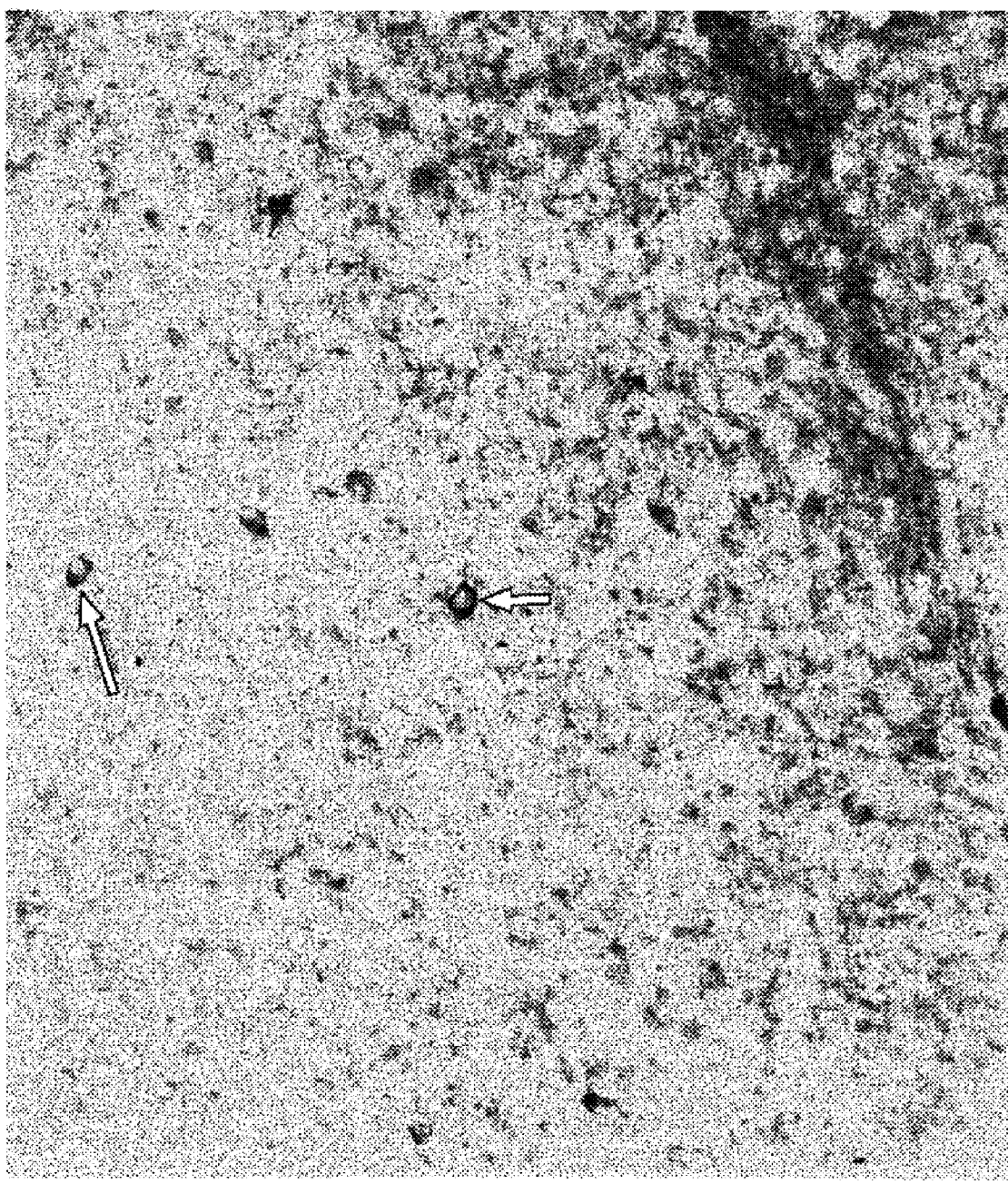

FIG. 5 shows a four month old wild-type mouse brain minimally positive for PHF-13 in the rostral portion of the amygdala. Cell bodies exhibit non-specific positivity (arrows) due to the secondary antibody.

Figure 6:
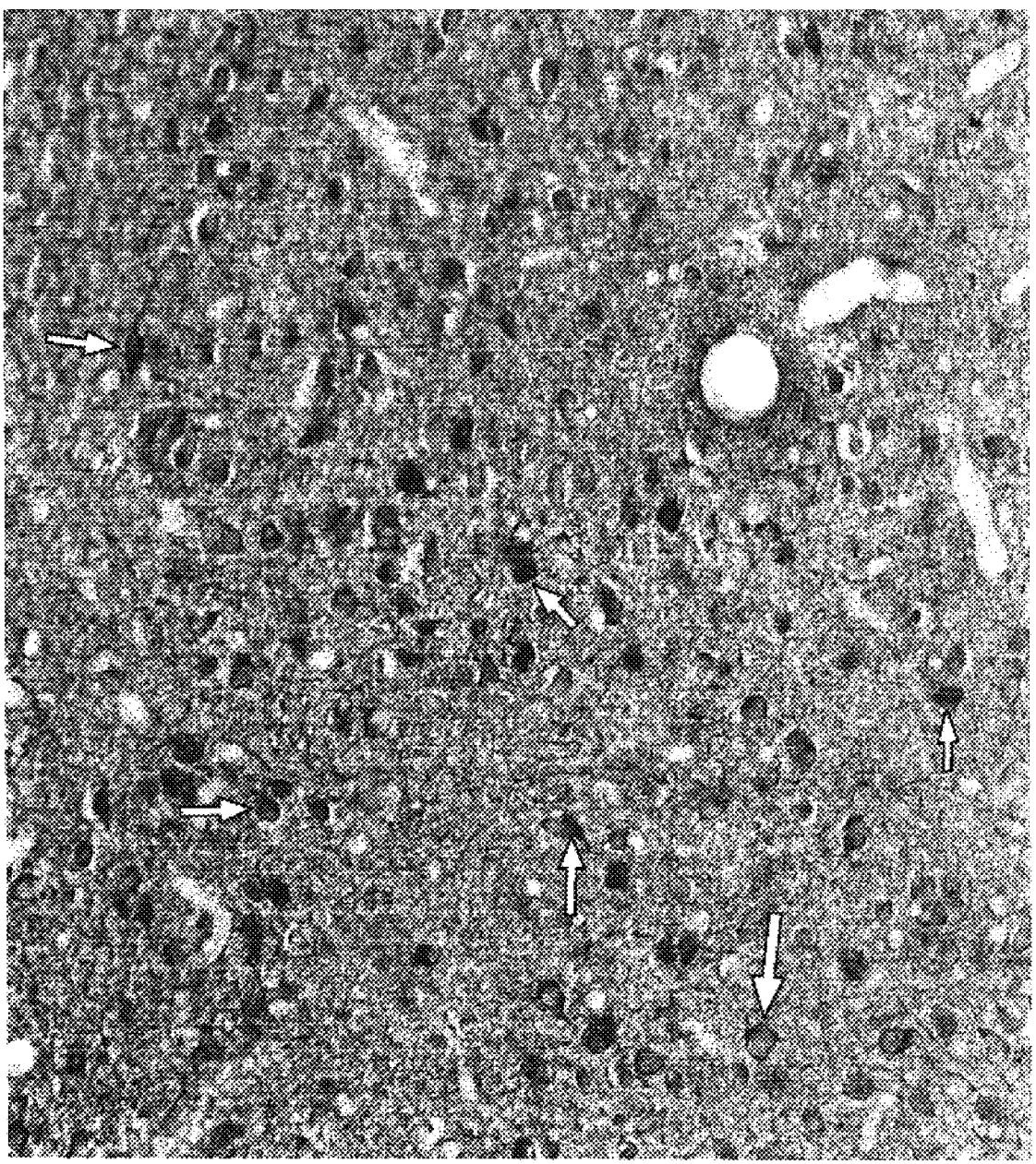

FIG. 6 shows a four month old transgenic mouse brain immunopositive for total tau (an antibody which recognizes total tau commercially available from Accurate Chemical and Scientific Corp Westbury, N.Y.) in several cell bodies of the rostral amygdala (examples marked by arrows).

Figure 7:
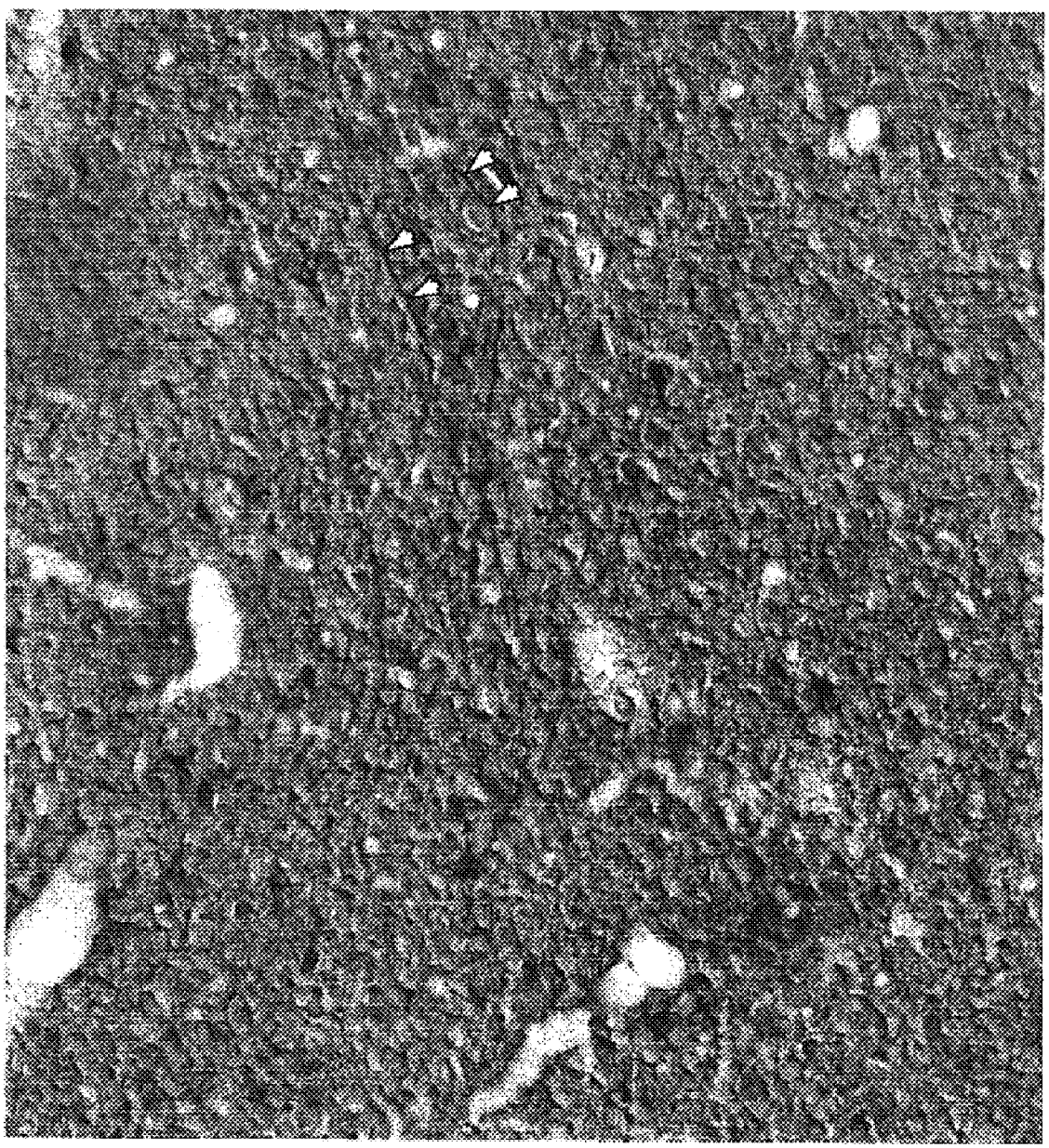

FIG. 7 shows a four month old wild-type mouse brain immunopositive for tau in axons (arrow heads) of the rostral amygdala.

Figure 8:
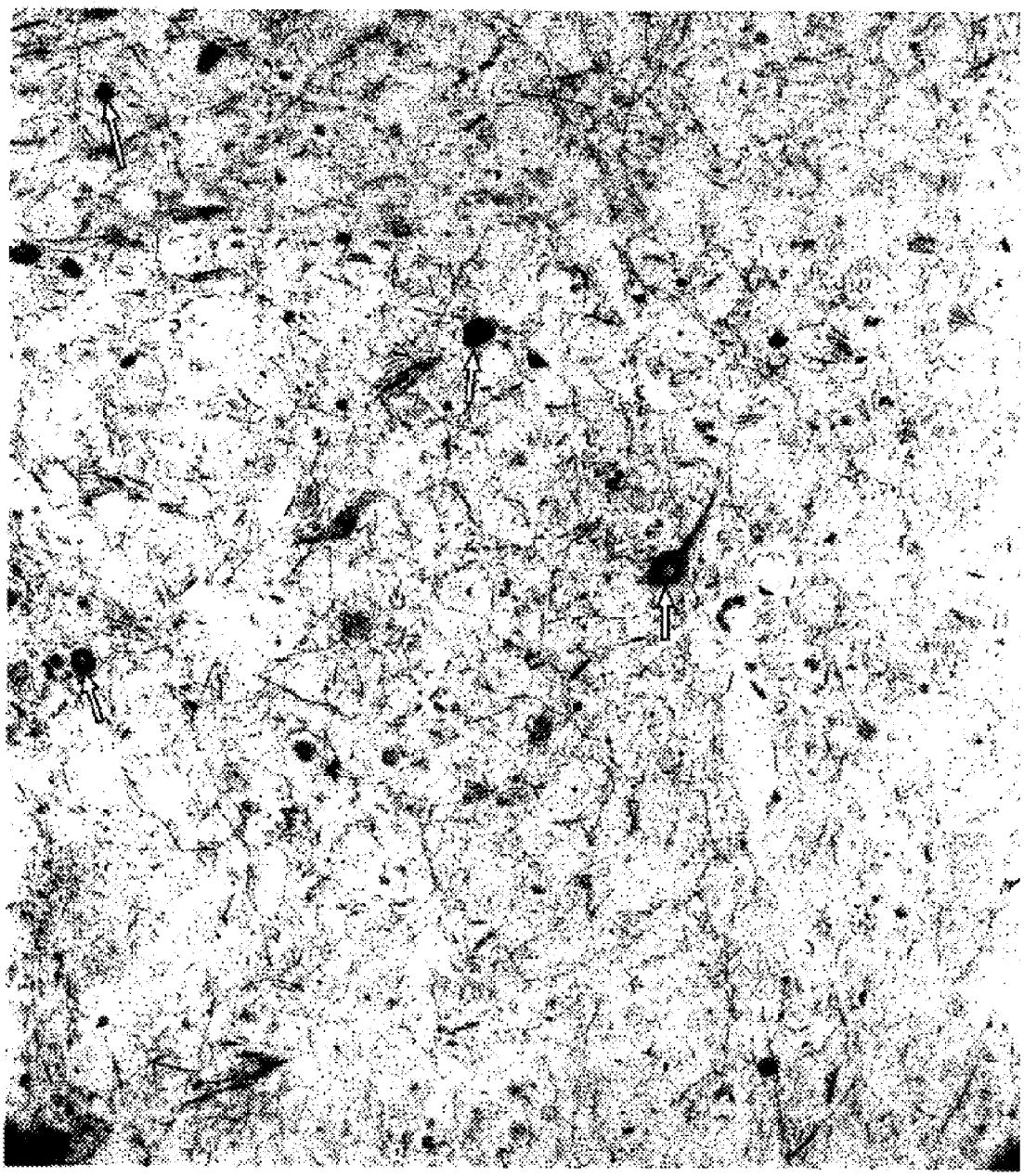

FIG. 8 shows a four month old transgenic mouse brain reacted with SMI-34 (a commercially available antibody which recognizes phosphorylated neurofilament H protein). Positive cells (arrows) are seen in the rostral amygdala.

Figure 9:
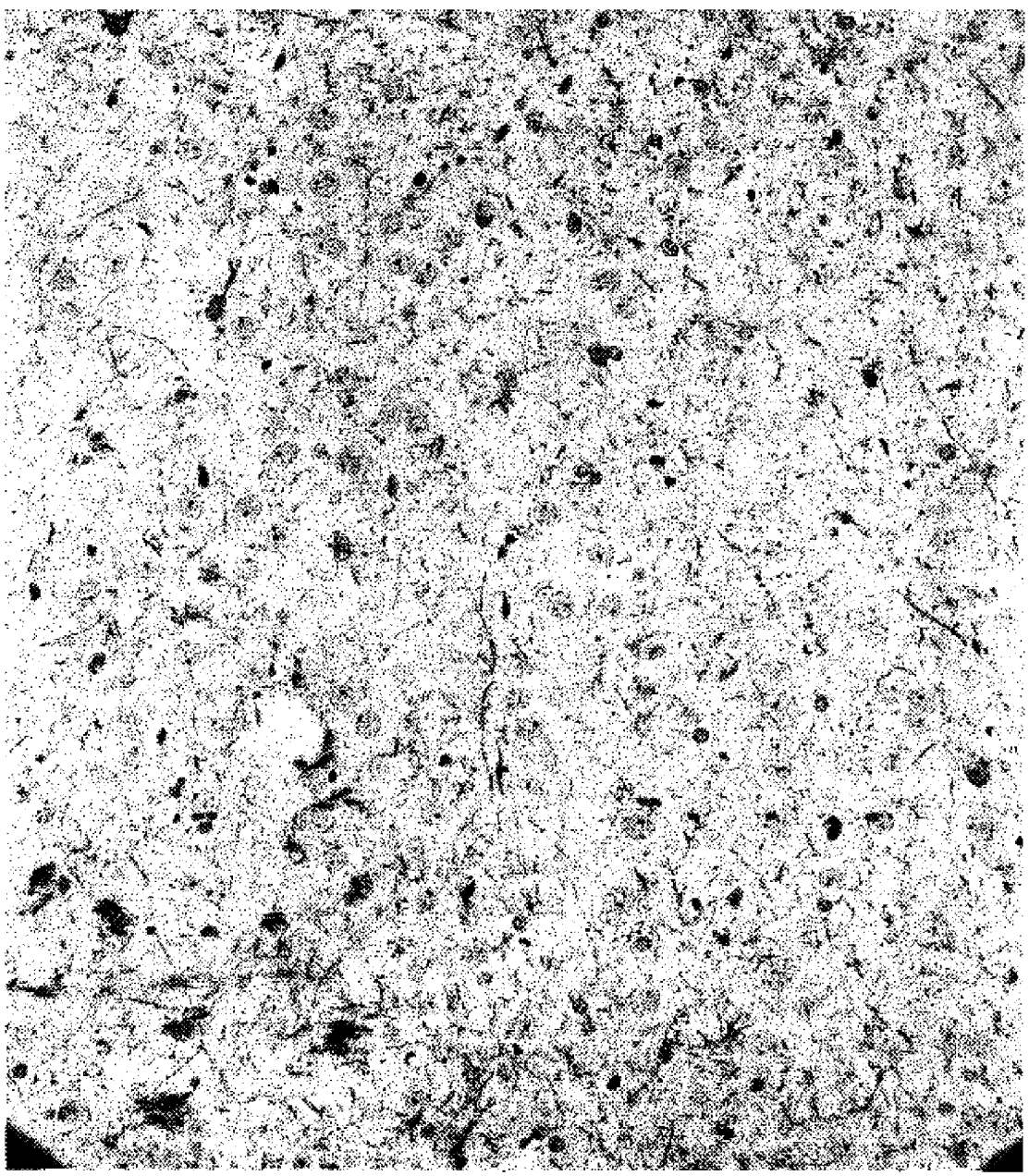

FIG. 9 shows minimal SMI-34 axonal positivity in the rostral amygdala of a four month old wild-type mouse brain.

Figure 10:
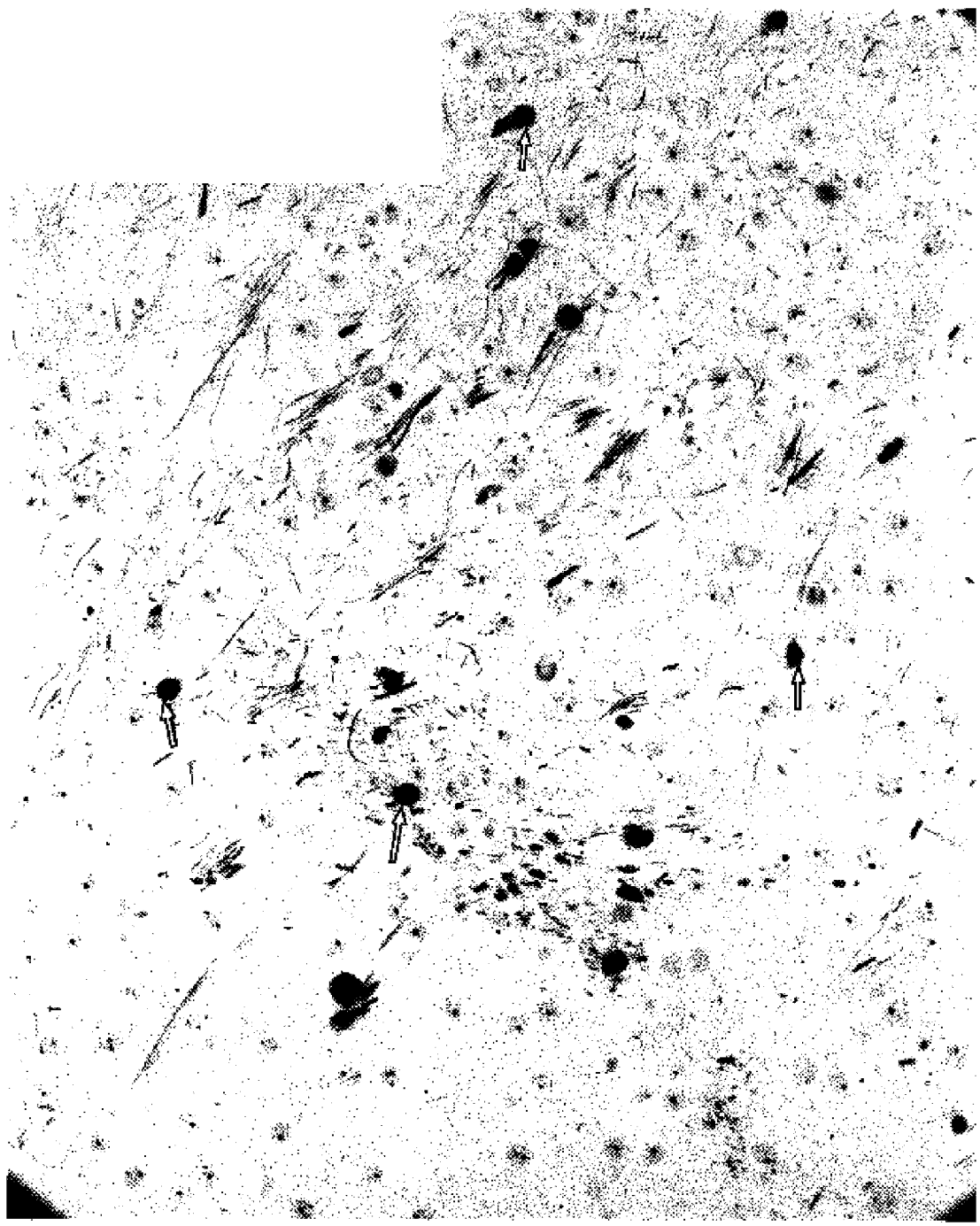

FIG. 10 shows silver-positive (an indication of disrupted cytoskeleton and neuronal cell death) cell bodies (arrows) in the rostral amygdala of a four month old transgenic mouse brain.

Figure 11:
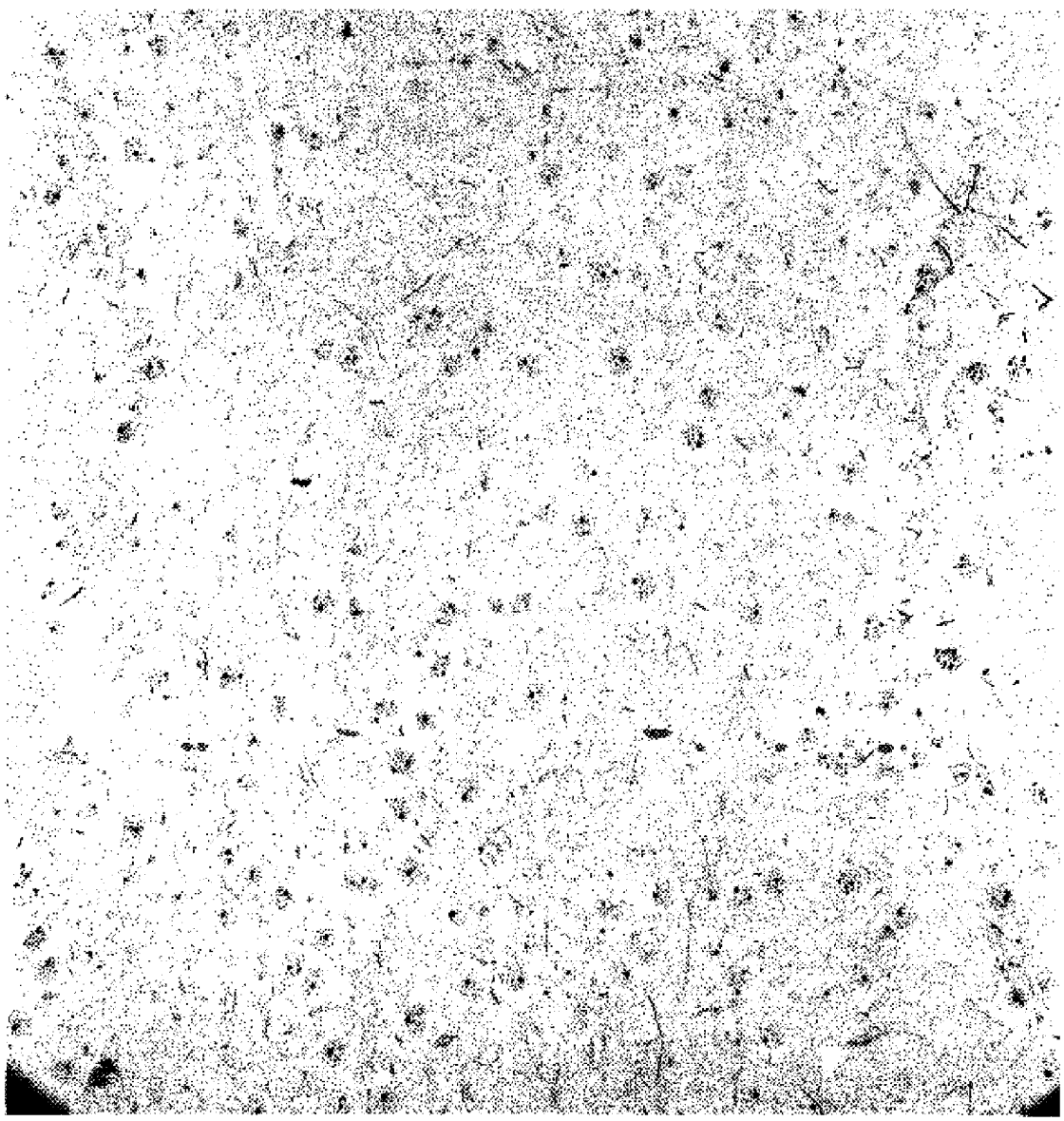

FIG. 11 shows minimal silver positivity of axons in the rostral amygdala of a four month old wild type mouse.

Figure 12:
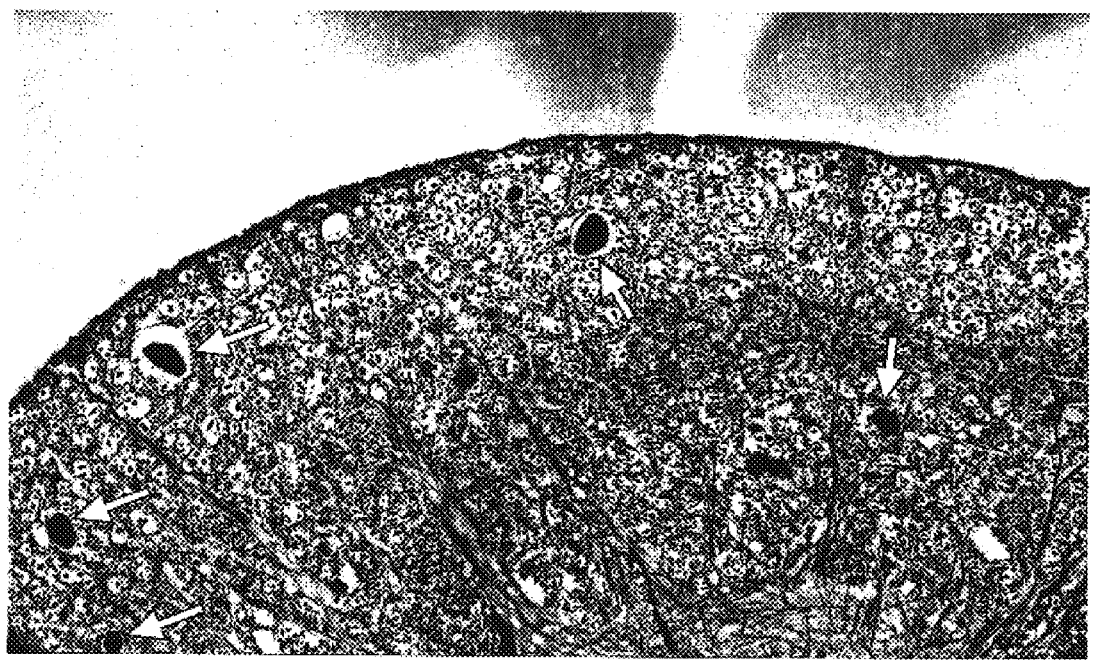

FIG. 12 shows several dilated axons (arrows) that exhibit silver positivity in the spinal cord of a five month old transgenic mouse.

Figure 13:
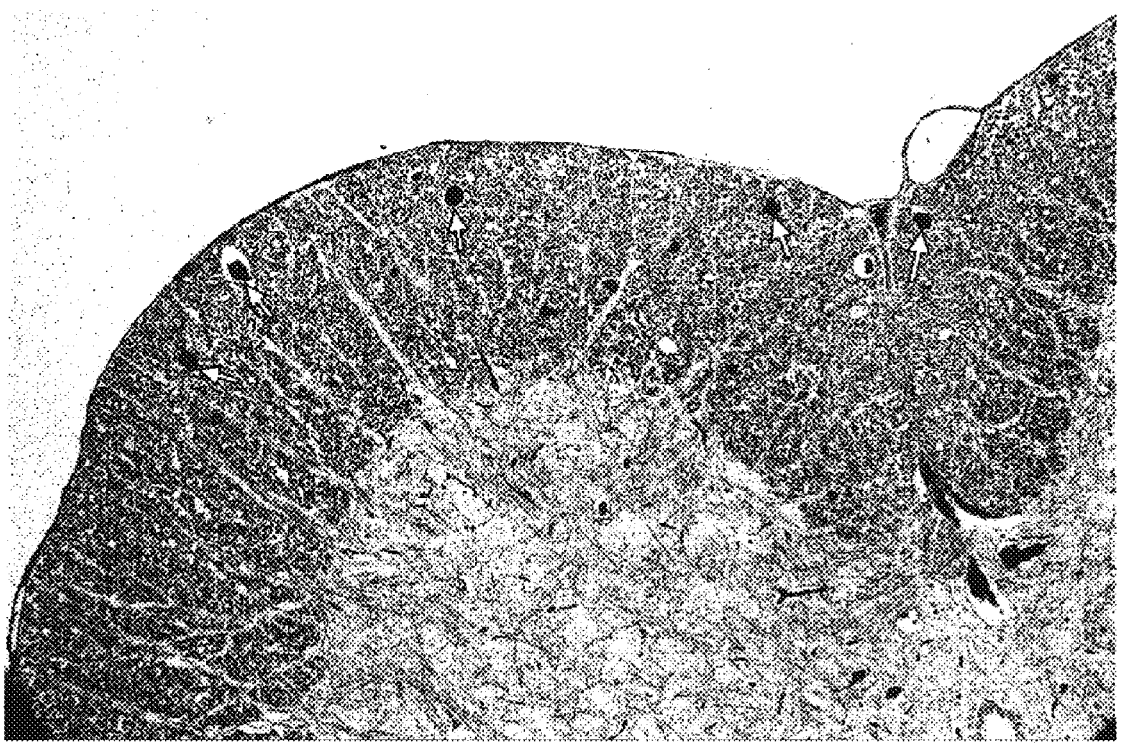

FIG. 13 shows several dilated axons (arrows) that exhibit SMI-34 positivity in the spinal cord of a five month old transgenic mouse.

Figure 14:
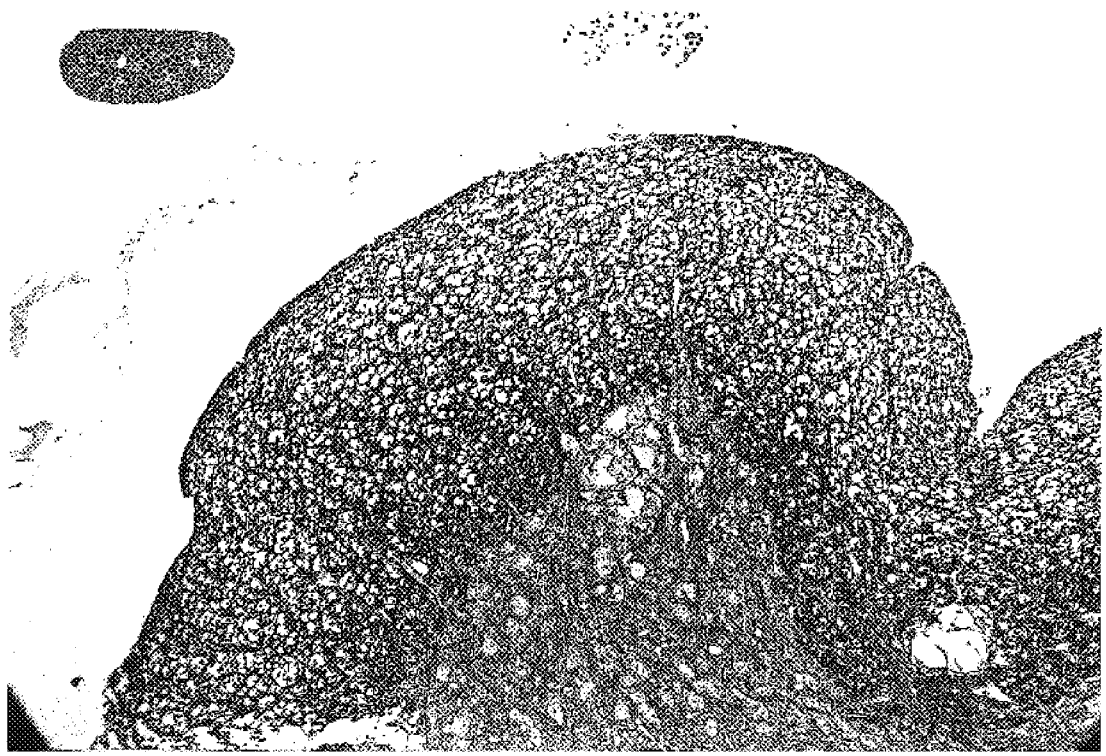

FIG. 14 shows that normal axons in the spinal cord of a six month old wild-type mouse are negative for SMI-34.

DETAILED DESCRIPTION

Generally, the nomenclature used herein and the laboratory procedures in cell culture, molecular genetics, nucleic acid chemistry and hybridization, biochemistry, histology and immunocytochemistry described below are those well known and commonly described in the art. Standard techniques are used for recombinant nucleic acid methods, polynucleotide synthesis, cell culture, transgene incorporation, Western blotting, immunocytochemistry and histological techniques such as silver staining. The techniques and procedures are generally performed according to conventional methods in the art and various general references which are provided throughout this specification. The procedures therein are well known in the art and are provided for the convenience of the reader. All the information contained therein is incorporated herein by reference.

In accordance with the foregoing objects, in one aspect of the invention are provided nonhuman animals harboring at least one copy of a transgene comprising a polynucleotide sequence that encodes a heterologous protein operably linked to regulatory elements that are capable of expressing the heterologous protein in the transgenic nonhuman animal. Said heterologous polypeptide is a truncated portion of the p35 cyclin dependent kinase 5 (cdk5) regulatory protein (27,28). The truncated heterologous polypeptide has the first 98 N-terminal amino acids removed and has a molecular weight of approximately 25,000 daltons. This novel polypeptide will be referred to as p25. Typically, the nonhuman transgenic animal is a mouse and the heterologous gene is the human p25 sequence. Transgenes are typically cDNA sequences that have been operably linked to cis-acting regulatory sequences that direct expression in the host transgenic mammal in cell-type specific manner, typically in neurons. Typically, the transgene will be incorporated into the host chromosomes in random, non-targeted fashion. The invention further provides that the nonhuman, transgenic animal harboring at least one copy of the heterologous p25 sequence transgene or gene targeting vector of the invention either non-homologously or homologously integrated into the chromosomal location express the p25 truncated polypeptide. Transgenic animals are typically produced by introduction of a transgene by microinjection into pronuclei of one-cell embryos or a targeting vector into the host by electroporation, lipofection, or viral transfection of embryonic stem (ES) cells. The transgenic animals that express the p25 polypeptide are suitable for use as models of disease and screening of potential therapeutic compounds including small molecules, proteins and polynucleotides. The invention also provides nonhuman or human cell lines to be derived by transformation of established cell lines or primary cell lines established directly from the nonhuman transgenic animal, for example neurons. It is obvious that the transgenic nonhuman animal can have additional genetic modifications by transgenic art or through traditional matings with other transgenic or naturally occurring animals to produce novel animals that serve as alternative disease models, drug screens or other applications. This includes the inactivation of the murine endogenous p35 gene through gene targeting in ES cells and resultant murine p35-deficient mice that becomes the preferred host for expression of the human p25 heterologous polypeptide. Such heterologous transgenes may be integrated in nonhomologous chromosomal locations in the transgenic animal, typically derived by pronuclear injection or may be integrated by gene targeting in ES cells by methods to inactivate the murine p35 gene and add linked sequences to direct expression of the heterologous human p25 sequences.

In general, the invention encompasses methods for the generation and characterization of transgenic animals that express the human p25 polypeptide, a proteolytic fragment of p35, both of which are an allosteric activators of cyclin dependent kinase 5 (cdk5). The transgenic animals express this human protein in the presence of the endogenous homologue. The techniques and procedures are performed according to established protocols that are generally considered to be routine methods in the art and references are provided within this specification. The protein kinase cdk5 when associated with an allosteric activator, e.g., p35 or p25 is reported in the literature to phosphorylate tau in vitro and in whole cells (see Background of the Invention). The transgenic mice thus produced establish the role of the human p25 in the formation of hyperphosphorylated tau in neurodegenerative conditions including Alzheimer's disease, Parkinson's disease, amyelolateral sclerosis, Huntington's chorea, stroke, traumatic brain injury, Pick's disease, neuraxonal dystrophy, multiple sclerosis, motor neuron disease, and spinocerebellar degeneration and other neurodegenerative diseases. It is apparent that the preparation of other transgenic animals that express the human p25 protein is easily accomplished including rats, hamsters, guinea pigs and rabbits. The transgenic animals that express the human p25 protein can be monitored for the level of expression and tau phosphorylation. It will be appreciated that under different conditions the level of expression and degree of tau phosphorylation will be inhibited in such an animal model. In particular, the screening of therapeutic agents that inhibit the activity of the human p25 protein will be greatly facilitated in animal models. It is apparent that the development of cell lines from the affected transgenic animals, (e.g., neurons) will improve the throughput in which biochemical and pharmacological analysis of the human p25 protein can be assessed.

Particularly preferred animal models for p25 overexpression are transgenic anmals which express p25 as described above. Such transgenic animals, particularly transgenic mice according to this invention, produce high quantities of p25 and hyperphosphorylated tau and neuronal death which may be detected according to the methods of the present invention. In accordance to this invention particular, the overexpression of p25 will be equal to or greater than endogenous p25 expression in such animals. Further, this level of p25 overexpression results in tau hyperphosphorylation which is minimal in wild type animals. With such elevated levels of p25, monitoring of hyperphosphorylation of tau and neuronal death is greatly facilitated. In particular, screening for compounds and other therapies for inhibiting tau phosphorylation are greatly simplified in animals overexpressing p25 according to this invention.

Agents are administered to test animals, such as test mice, which are transgenic and which overexpress p25. Particular techniques for producing transgenic mice which overexpress p25 are described below. It will be appreciated that the preparation of other transgenic animals overexpressing p25 may easily be accomplished, including rats, hamsters, guinea pigs, rabbits, and the like. In light of this disclosure, the effect of test compounds on the hyperphosphorylation of tau in the test animals may be measured in various specimens from the test animals.

The effect of test agents on hyperphosphorylation of tau may be measured in various specimens from the test animals. In all cases, it will be necessary to obtain a control value which is characteristic of the level of tau phosphorylation and neuronal death in the test animal in the absence of the test compound(s). In cases where the animal is sacrificed, it will be necessary to base such control values on an average or a typical value from other test animals which have been transgenically modified to overexpress p25 but which have not received the administration of any test compounds or any other substances expected to affect the level of tau phosphorylation or neuronal death. Once such control level is determined, test compounds can be administered to additonal test animals, where deviation from the average control value indicates that the test compound had an effect on the tau phosphorylation or neuronal death in the animal. Test substances considered positive, i.e., likely to be beneficial in the treatment of AD or other neurodegenerative diseases, will be those which are able to reduce the level of tau phosphorylation or neuronal death preferably by at least 20% and most preferably by 80%. In addition there may be paired helical or straight filament formation in transgenic animals which overexpress p25 and display tau hyperphosphorylation. In these cases, test compounds can be administered to test animals and the reduction of filament formation monitored as a result of exposure to the compound. In addition, there may be behavioral alterations in the transgenic animals which overexpress p25 and display tau hyperphosphorylation. In these cases it will be necessary to obtain a control value from live animals performing a behavioral task (e.g., the measurement of locomotor activity) in the test animal in the absence of test compound(s). Such a control will also be determined in non-transgenic, wild type mice. The difference between the wild type and transgenic mice will serve as the outcome measure for the effects of compounds. Once such control levels are determined, test compounds can be administered to additional test animals, where reduction in or reversal of the difference between the wild type and transgenic mice indicates that test compound has an effect on the behavioral test being measured. Test substances considered positive, i.e., likely to be beneficial in the treatment of AD or other neurodegenerative diseases, preferably will be those which are able to reverse or, substantially reverse, or favorably modify the behavioral abnormality in the transgenic animal to the level found in wild type mice.

Test agents will be defined as any small molecule, protein, polysaccharides, deoxy or ribomucleotides, or any combination thereof that when added to the cell culture or animal will not adversely interfere with the cell or animal viability. Agents that alter the level of human p25 expression and tau phosphorylation will be considered as candidates for further evaluation as potential therapeutics. The test compound will typically be administered to transgenic animals at a dosage of from 1 ng/kg to 100 mg/kg, usually from 10 ug/kg to 32 mg/kg.

Test compounds which are able to inhibit phosphorylation of tau are considered as candidates for further determinations of the ability to block tau phosphorylation in animals and humans. Inhibition of tau phosphorylation indicates that cdk5/p25 activity has been at least partly blocked, reducing the amount of cdk5/p25 available to phosphorylate tau.

The present invention further comprises pharmaceutical compositions incorporating a compound selected by the above-described method and including a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compound or compounds to an intended host. Sterile water, alcohol, fats, waxes and inert solids may be used as the carrier. Pharmaceutically acceptable adjuvants, buffering agents, dispersing agents, and the like may also be incorporated into the pharmaceutical compositions. Preparation of pharmaceutical compositions incorporating active agents is well described in the medical and scientific literature. See, for example, Remington's Pharmaceutical Sciences, Mack Publishing Company, Easton, Pa., $16^{th}$ Ed., 1982, the disclosure of which is incorporated herein by reference.

The pharmaceutical compositions just described are suitable for systemic administration to the host, including both parenteral, topical, and oral administration. The pharmaceutical compositions may be administered parenterally, i.e., subcutaneously, intramuscularly or intravenously. Thus, the present invention provides compositions for administration to a host where the compositions comprise a pharmaceutically acceptable solution of the identified compound in an acceptable carrier, as described above.

Commercial Research and Screening Uses

Non-human animals comprising transgenes which encode p25 can be used commercially to screen for agents having the effect of preventing or reducing the phosphorylation of tau and neuronal death. Such agents can be developed as pharmaceuticals for treating hyperphosphorylation of tau and AD amongst other neurodegenerative diseases. For example, the p53 knockout mice of Donehower et al. (54) have found wide acceptance as commercial prouducts for carcinogen screening and the like. The transgenic animals of the present invention exhibit abnormal tau phosphorylation and can be used for pharmaceutical screening and as disease models for neurodegenerative diseases and cdk5/p25 and tau biochemistry. Such animals have many uses including but not limited to identifying compounds that affect tau hyperphosphorylation; in one variation, the agents are thereby identified as candidate pharmaceutical agents. The transgenic animals can also be used to develop agents that modulate cdk5 or p25 expression and or stability; such agents can serve as therapeutic agents to treat neurodenerative diseases. The p25 overexpressing mice of the invention can also serve as disease models for investigating tau-related pathologies (e.g., AD, Pick's disease, Parkinson's disease, frontal temporal lobe dementia associated with chromosome 17, stroke, traumatic brain injury, mild cognitive impairment and the like). Such transgenic animals can be commercially marketed to researchers, among other uses.

Having described the invention in general terms, reference is now made to specific examples. It is to be understood that these examples are not meant to limit the present invention, the scope of which is to be determined by the appended claims.

EXPERIMENTAL EXAMPLES

The plasmids

The plasmid pNSE-p25 (rat neuron specific enolase promoter, human p25 transgene) contains DNA from 4 different sources: the rat neuron specific enolase promoter; the human cDNA for the p25 catalytic fragment of the p35 protein; the SV40 polyadenylation signal sequence and a commercially available plasmid vector. The transgene is isolated by BamH1 restriction enzyme digestion of pNSE-p25. This restriction digest releases the NSE-p25 transgene (3212 bp) from the plasmid cloning vector pSP72 (2462 bp) (Promega, Madison, Wis.). The rat Neuron Specific Enolase (NSE) promoter sequence is 1826 bp (SEQ ID NO: 1) and has been demonstrated to efficiently express DNA coding sequences in neurons of transgenic mice (55). The coding region for the human p25 sequence is 633 bp. (SEQ ID NO: 2). The 3-prime untranslated and SV40 polyadenylation sequence are 688 bp (SEQ ID NO: 3). The microinjected NSE-p25 transgene is 3212 bp (SEQ ID NO: 4). Enzymatic reactions of recombinant DNA, including ligations, restriction endonuclease digestions, DNA synthesis reactions, single strand fill-in reactions, and bacterial transformations performed are well established procedures as described by Sambrook, J., Fritsch, E. F. and Maniatis, T. Molecular Cloning: A Laboratory Manual. 2nd edition, Cold Spring Harbor Press, New York, 1989.

The SV 40 polyadenylation sequence (SEQ ID NO: 3) was cloned into the commercially available plasmid pSP72 (SEQ ID NO: 5) at Xba1 and BstX1 sites. This plasmid, designated pSP-SVpA, served as the backbone vector for the construction of the NSE-p25 transgene plasmid. The cDNA for the human p25 catalytic fragment was derived using polymerase chain reaction (PCR). The human p35 full length cDNA was used as the template for amplification of the p25 insert. We received the p35 template DNA from Dr. David Auperin of Pfizer; the human p35 sequence was cloned into the EcoR1 site of the pFastBac1, baculoviral expression vector (Gibco-BRL, Gaithersburg, Md.). The PCR primers were designed to have Not1 restriction sites outside the coding sequence to facilitate transgene construction. The forward primer also introduced a new ATG start codon adjacent to the GCC (Ala codon at position 99 of the human p35 sequence). The primers (submitted in 5-prime to 3-prime orientation) were p25-forward: GCGGCCGCATG-GCCCAGCCCCCACCGGCCCAGCCGCCTGCA (SEQ ID NO: 6) and p25-reverse: CTCCTCCTAGGC-CTGGAATCGG*TGA*GGCGGCCGC (SEQ ID NO: 7). The ATG is introduced start codon, the *TGA* is the stop codon and the GCGGCCGC are the Not1 restriction sites added to the PCR primers. The resulting PCR product is 648 bp containing the entire 633 bp human p25 cDNA sequence with engineered ATG start site (SEQ ID NO: 2) and an additional 15 bp from addition of the Not 1 cloning sites. The 648 bp fragment was subcloned into the pCR2.1 (Invitrogen, Carlsbad, Calif.) vector for verification of sequence prior to use as insert in the final transgene. The confirmed 648 bp Not 1 fragment was ligated into the Not 1 restriction site of pSP-SVpA producing the plasmid pSP-SVpA:p25. The rat Neuron Specific Enolase (NSE) promoter was isolated from the plasmid pNSE-lacZ obtained from Dr. J. G. Sutcliffe of the Research Institute of Scripps Clinic (LaJolla, Calif.). The rat NSE promoter sequence (SEQ ID NO: 1) was isolated by EcoR1 and Hind III restriction digestion of the pNSE-lacZ plasmid. The 1.8 kb fragment was extracted by agarose gel electrophoresis and purified. The 5-prime single strand overhangs generated by the restriction enzymes were filled by Klenow reaction to produce the rat NSE promoter fragment with double stranded blunt ends. The 1826 bp rat NSE blunt end promoter fragment was blunt end ligated into the Sma 1 restriction site of pSP-SVpA:p25. The correct orientation of the rat NSE promoter within the pSP-SVpA:p25 was verified by double restriction digests of BamH1 and Xho1. Plasmids with the correct orientation were assigned the designation as pNSE-p25. The entire sequence of the 3212 bp NSE-p25 transgene (SEQ ID NO: 4) was analyzed and verified by automated sequencing on ABI 373 sequencer (Foster City, Calif.) using the standard dye-terminator chemistry protocol outlined by ABI. All plasmids were grown in DH5alpha bacterial cells (Gibco BRL Gaithersburg Md.).

Production of Transgenic Mice Overexpressing Human p25

The 3212 bp NSE-p25 transgene DNA fragment was excised from the pNSE-p25 plasmid by BamH1 restriction endonuclease reaction. The 3.2 kbp fragment was isolated by electroelution (50V, 3 hrs) after electrophoresis in 1% agarose gel (FMC Bioproducts, Rockland Me.). The fragment was further purified by on a Schleicher and Schuell (Keene, N.H.) Elutip-d column following protocols established by the manufacturer for DNA purification prior to murine embryo microinjection.

Production of transgenic mice by pronuclear microinjection was carried out by published procedures as outlined in Hogan, B. et al Manipulating the Mouse Embryo: A Laboratory Manual 2nd edition, Cold Spring Harbor Laboratories, New York, 1994. Pronuclear stage embryos from F1 females mice of the strain FVB/N (Charles River Labs, Wilmington, Mass.) were obtained after superovulation with 5 international units (IU) of follicle stimulating hormone from pregnant mare serum (Sigma St Louis, Mo.) and 2.5 I.U. human chorionic gonadotropin (Sigma). The actual microinjection procedure was performed as described by Wagner, T. et al. (56) except that the embryos were transferred immediately to pseudopregnant CD-1 recipient females (Charles River Laboratories, Wilmington, Mass.) for development of embryos to term. Mice resulting from the reimplantation events were tested for the presence of the NSE-p25 transgene by PCR analysis of genomic DNA isolated from tail biopsies at 3 weeks of age. The mice that demonstrated positive for the presence of the NSE-p25 transgene were mated with wild type FVB/N mice (Charles River Laboratories, Wilmington, Mass.) of the opposite sex. Offspring of these matings were tested for germline transmission by PCR analysis or Southern blot analysis of genomic DNA isolated from tail biopsies at 3 weeks of age. Transgenic lines were produced from 7 founder transgenic mice and were maintained by breeding to wild type FVB/N mice and PCR genotyping for the presence of the NSE-p25 transgene.

The experiments described below were done in mice heterozygous for the inserted transgene. These mice were derived by breeding mice positive for the transgene insert with FVB/N wild-type animals and screening offspring by PCR for presence of the NSE-p25 transgene sequences.

Detection of Overexpression of p25 Protein
Western Blot

Whole brains from 1 or 4 month old transgenic (Tg) and wild type (wt) mice were removed and snap frozen in liquid nitrogen. Amygdala, thalamus and cortex were dissected and homogenized in 1 ml of lysis buffer (as described in 37). The samples were boiled for 10 minutes and then centrifuged at 13,000 rpm. Protein concentrations of the resulting supernatants were determined by the Pierce BCA method (BCA micro protein assay, catalog #23225, Pierce, Rockford Ill.). Ten micrograms of each sample were electrophoresed on an SDS polyacrylamide gel (57) and transferred to ProBlott protein paper for western blot analysis [Western blotting protocols, ECL detection, Amersham Life Science Arlington Heights, Ill. (1995)]. Non specific sites were blocked by incubating the blots in 5% nonfat milk in tris-buffered saline (20 mM Tris Base, 127 mM NACl, 3.8 mM HCl pH 7.6, Sigma) included 0.1% tween-20 (TBS-T). Primary antibodies were diluted in 5% nonfat milk\TBS-T. The blots were placed in the diluted antibody solutions and rotated for 1 hr at 23° C. The western blots were then washed for 30 min in TBS-T. Secondary horseradish peroxidase linked antibodies were diluted in 5% nonfat milk\TBS-T. The blots were incubated with the secondary antibody solution and rotated for 45 min at 23° C. The blots were then washed for 30 min in TBS-T. Equal volumes of Amersham's ECL developing solutions A and B were mixed together. The Western blots were incubated for 1 min in the developing solution. The blots were wrapped in Saran® wrap and then exposed to imaging film (Kodak Rochester N.Y. X-OMAT AR, catalog #165 1454).

Figure 1:
FIG. 1A. Western blots of the amygdala (1), thalamus (2) and cortex (3) from 3 wild type mice were probed with an antibody specific for p25 and p35/39 (generous gift of L.-H. Tsai, Harvard Medical School Cambridge, Mass.).
FIG. 1B, Western blots of the amygdala (1), thalamus (2) and cortex (3) from 3 p25 transgenic mice were probed with the same antibody as in FIG. 1A.

Western blots of the amygdala (1), thalamus (2) and cortex (3) from 3 mice were probed with an antibody specific for p25 and p35/39 (gift of L.-H. Tsai, Harvard Medical School, FIG. 1A). While detection of p35/39 is apparent, no p25 is detected in wild type mice. When the same analysis is performed in the transgenic mice (FIG. 1B), robust expression of p25 in addition to the constitutive expression of p35 is detected. These results confirm that expression of the transgene is robust in the p25 transgenic animals.

Silver Stain & SMI 34 Immunohistochemistry

Tissues collected from scheduled sacrifice mice were perfusion-fixed in situ with 10% neutral-buffered formalin or 4% paraformaldehyde, whereas tissues collected from mice found dead were immersion fixed in formalin. Following fixation, trimmed tissues were dehydrated through graded alcohols and embedded in paraffin. Standard cross sections of brain were identified by analogy to figures in *The Mouse Brain in Stereotaxic Coordinates* (Franklin and Paxinos, 1997). Paraffin sections (8 μm thick) were stained with modified Bielschowsky silver stain and, immunohistochemically, with an antibody directed against phosphorylated neurofilament (SMI 34, commercially available from Sternberger Monoclonals, Inc Lutherville, Md.).

Immunohistochemistry

For immunohistochemical studies, transgenic and wild type mice were deeply anesthetized with sodium pentobarbital (60 mg/kg, i.p.) and perfused through the ascending aorta with 20 ml of 0.1 M $NaPO_4$ containing 0.9% NaCl (PBS, 7.4) followed by 30 ml of fixative containing 4% paraformaldehyde in 0.1 M $NaPO_4$ (PB, 7.4) buffer. The brains were removed, cryoprotected for 48 hr in PBS containing 20% sucrose, frozen in a bed of pulverized dry ice, and then cut into 35 micron sections on a sliding microtome. Consecutive 1 in 18 series of sections were collected in 0.1M PB and processed for immunohistochemistry as described below.

For immunohistochemistry, sections were incubated for 1 hr in 50 mM Tris buffer, ph 7.4 containing 0.9% NaCl (TBS) and 0.1% Triton X-100. The sections were then washed in TBS and incubated for 1 hr in antibody vehicle (4% goat or horse serum, 0.1% Triton X-100 in TBS). After additional washes in TBS, sections were incubated overnight at 4° C. in vehicle containing the primary antibody.

Following overnight incubation in the primary antibody, sections were washed in TBS, incubated for 1 hr in vehicle containing biotinylated horse anti-mouse or goat anti-rabbit antibody (as per manufacturer, Vector Labs, Burlingame, Calif.), washed in TBS, and then incubated for 1 hr in TBS containing ABC/horseradish peroxidase reagent (Vector Labs, Burlingame, Calif.).

After additional washes in TBS, immunolocalization products were visualized by developing sections for 3–5 min in 50 mM Tris buffer (pH 7.6) containing 0.04% diaminobenzdine (DAB) and 0.003% $H_2O_2$. Sections were subsequently washed in the Tris buffer, mounted onto slides and dehydrated and coverslipped using DPX (Fluka, Ronkokoma, N.Y.).

Antibodies

AT-8:
Used at 1:1,000 (200 ng/ml), mouse monoclonal which recognizes ser 202 and thr 205 of human phosphorylated tau. (Innogenetics, Inc. Zwij+ndrecht (Belgium))

PHF-13:
Used at 1:20,000, mouse monoclonal which recognizes ser 396 and thr 404 of human phosphorylated tau. (Gift from V. Lee, University of Pennsylvania)

anti-TAU:

Used at 1:7,000, rabbit polyclonal which recognizes total tau. (Accurate Chemical and Scientific Corp Westbury, N.Y.).

SMI 34:

Used at 1:1000, mouse monoclonal which recognizes phosphorylated neurofilament.H (Sternberger Monoclonals, Inc., Lutherville Md.)

Brains from four month old transgenic and wild type mice were compared for the presence of tau and neurofilament phosphoepitopes by immunohistochemistry. AT-8 and PHF-13, monoclonal antibodies which recognize phosphorylated Ser-202 and Thr-205, and Ser-396,404, respectively, labeled neurons in amygdala (FIGS. 2 and 4, respectively), thalamus/hypothalamus and cortex adjacent to external capsule (not shown) of transgenic animals but not in corresponding regions of wild-type animals (FIGS. 3 and 5). In addition, staining for total tau revealed numerous cell bodies in p25 transgenic animals (FIG. 6) while mostly axons and very few cell bodies were labeled in wild type mice (FIG. 7). A monoclonal antibody (SMI34) recognizing phosphorylated neurofilament H also showed increased immunostaining in these three brain regions and spinal cord of transgenic mice (amygdala is depicted in FIG. 8), but not in wild type (FIG. 9). All three of these markers are known to be increased in Alzheimer brain relative to age-matched control.

In Alzheimer's brain, pathological changes in neurons containing altered tau proteins have classically been identified using silver-based staining methods. We found that, in the transgenic mice of this invention, neurons in the same three brain regions described above and spinal cord show positive labelling using the modified Bielschowsky silver stain (amygdala, FIG. 10). This staining was once again absent in wild-type control animals (FIG. 11). We also detected increases in silver staining and phosphorylated neurofilament H in obviously enlarged axons in the spinal cord of transgenic mice (FIGS. 12 and 13, respectively), while in wild type mice, axons were of the expected diameter and neurofilament staining was normal (FIG. 14).

With regard to AT-8 immunoreactivity, most labelled neurons in the amygdala exhibited well-defined, densely staining soma, often with a swollen, dystrophic hillock and contorted axon (FIG. 2). Less commonly, diffuse labelling of unidentified cells was seen, and occasionally cells having astroglial or microglial morphology were labelled. In cortex adjacent to external capsule, the majority of AT-8 staining was found in intensely-labelled neuronal cell bodies, often accompanied by axons when present in the plane of the section. Thalamic/hypothalamic staining was more diverse, including both neuronal staining as seen in other sections.

Histologic examination of brain and spinal cord from p25 Tg mice revealed changes in neurons and axons of brain or spinal cord (n=19) but not in these tissues from 10 age-matched, wild-type controls. Axonal changes were most pronounced in the spinal cord (cervical and thoracic) and consisted of marked dilation of axoplasm to diameters of 20 to 50 μm. Dilated axons were filled with both silver staining and phosphorylated neurofilament H (FIGS. 12, 13). A given cross section of affected cord generally contained between 10 and 100 overtly dilated axons distributed among all funiculi of white matter. Luxol fast blue staining illustrated dissolution of the internal portion of myelin sheath of affected axons (not shown).

OTHER PUBLICATIONS

(45) Baumann, K., E. M. Mandelkow, et al. (1993). "Abnormal Alzheimer-like phosphorylation of tau-protein by cyclin-dependent kinases cdk2 and cdk5." FEBS Letters 336(3): 417–24.

(32) Bazan, J. F. (1996). "Helical fold prediction for the cyclin box." Proteins 24(1): 1–17.

(9) Biernat, J., N. Gustke, et al. (1993). "Phosphorylation of Ser262 strongly reduces binding of tau to microtubules: distinction between PHF-like immunoreactivity and microtubule binding." Neuron 11 (1): 153–63.

(6) Biernat, J., E. M. Mandelkow, et al. (1992). "The switch of tau protein to an Alzheimer-like state includes the phosphorylation of two serine-proline motifs upstream of the microtubule binding region." EMBO Journal 11(4): 1.593–7.

(17) Billingsley, M. L. and R. L. Kincaid (1997). "Regulated phosphorylation and dephosphorylation of tau protein: effects on microtubule interaction, intracellular trafficking and neurodegeneration." Biochemical Journal 323(Pt 3): 577–91.

(7) Bramblett, G. T., M. Goedert, et al. (1993). "Abnormal tau phosphorylation at Ser396 in Alzheimer's disease recapitulates development and contributes to reduced microtubule binding." Neuron 10(6): 1089–99.

(31) Brown, N. R., M. E. Noble, et al. (1995) "The crystal structure of cyclin A." Structure 3(11): 1235–47.

(36) Chae, T., Y. T. Kwon, et al. (1997). "Mice lacking p35, a neuronal specific activator of Cdk5, display cortical lamination defects, seizures, and adult lethality." Neuron 18(1): 29–42.

(54) Donehower, L. A., M. Harvey, et al. (1992). "Mice deficient for p53 are developmentally normal but susceptible to spontaneous tumours." Nature 356(6366): 215–21.

(55) Forss-Petter, S., P. E. Danielson, et al. (1990). "Transgenic mice expressing beta-galactosidase in mature neurons under neuron-specific enolase promoter control." Neuron 5(2): 187–97.

Franklin and Paxinos, "The Mouse Brain in Stereotaxic Coordinates", 1997.

(11) Goedert, M., R. Jakes et al. (1996) "Assenbly of microtubule-associated protein tau into Alzheimer-like filaments induced by sulphated glycosaminoglycans." Nature 383:550–553.

(2) Goedert, M. (1997). "The Neurofibrillary Pathology of Alzheimer's Disease." The Neuroscientist 3(2): 131–141.

(3) Goedert, M., R. A. Crowther, et al. (1998). "Tau mutations cause frontotemporal dementias." Neuron 21(5): 955–958.

(5) Gustke, N., B. Steiner, et al. (1992). "The Alzheimer-like phosphorylation of tau protein reduces microtubule binding and involves Ser-Pro and Thr-Pro motifs." FEBS Letters 307(2): 199–205.

(44) Hasegawa, M., R. A. Crowther, et al. (1997). "Alzheimer-like changes in microtubule-associated protein Tau induced by sulfated glycosaminoglycans. Inhibition of microtubule binding, stimulation of phosphorylation, and filament assembly depend on the degree of sulfation." Journal of Biological Chemistry 272(52): 33118–24.

Hogan, B. et al. "Manipulating the Mouse Embryo: A Laboratory Manual", 2nd ed., Cold Spring Harbor Laboratories, New York, 1994.

(22) Hong, M., D. C. Chen, et al. (1997). "Lithium reduces tau phosphorylation by inhibition of glycogen synthase kinase-3." Journal of Biological Chemistry 272(40): 25326–32.

(15) Hong, M., V. Zhukareva, et al. (1998). "Mutation-Specific Functional Impairments in Distinct Tau Isoforms of Hereditary FTDP-17." Science 282: 1914–1917.

(14) Hutton, M., C. L. Lendon, et al. (1998). "Association of missense and 5'-splice-site mutations in tau with the inherited dementia FTDP-17." Nature 393(6686): 702–5.

(16) Imahori, K. and T. Uchida (1997). "Physiology and pathology of tau protein kinases in relation to Alzheimer's disease." Journal of Biochemistry 121(2): 179–88.

(18) Ishiguro, K., M. Takamatsu et al. (1992). "Tau protein kinase I converts normal tau protein into A68-like component of paired helical filaments." Journal of Biological Chemistry 267:10897–901.

(10) Kampers, T., P. Friedhoff, et al. (1996). "RNA stimulates aggregation of microtubule-associated protein tau into Alzheimer-like paired helical filaments." FEBS Letters 399(3): 344–9.

(57) Laemmli, U. K. (1970). "Cleavage of structural proteins during the assembly of the head of bacteriophage T4." Nature 227(259): 680–5.

(51) Lee, K. Y., C. C. Helbing, et al. (1997). "Neuronal Cdc2-like kinase (Nclk) binds and phosphorylates the retinoblastoma protein." Journal of Biological Chemistry 272(9): 5622–6.

(28) Lew, J., Q. Q. Huang, et al. (1994). "A brain-specific activator of cyclin-dependent kinase 5." Nature 371 (6496): 423–6.

(46) Lew, J., R. J. Winkfein, et al. (1992). "Brain proline-directed protein kinase is a neurofilament kinase which displays high sequence homology to p34cdc2." Journal of Biological Chemistry 267(36): 25922–6.

(20) Lovestone, S., C. L. Hartley, et al. (1996). "Phosphorylation of tau by glycogen synthase kinase-3 beta in intact mammalian cells: the effects on the organization and stability of microtubules." Neuroscience 73(4): 1145–57.

(8) Mandelkow, E. M., J. Biernat, et al. (1995). "Tau domains, phosphorylation, and interactions with microtubules." Neurobiology of Aging 16(3): 355–62; discussion 362–3.

(49) Matsubara, M., M. Kusubata, et al. (1996). "Site-specific phosphorylation of synapsin I by mitogen-activated protein kinase and Cdk5 and its effects on physiological functions." Journal of Biological Chemistry 271(35): 21108–13.

(23) Michel, G., M. Mercken, et al. (1998). "Characterization of tau phosphorylation in glycogen synthase kinase-3beta and cyclin dependent kinase-5 activator (p23) transfected cells." Biochimica et Biophysica Acta 1380(2): 177–82.

(40) Nikolic, M., M. M. Chou, et al. (1998). "The p35/Cdk5 kinase is a neuron-specific Rac effector that inhibits Pak1 activity." Nature 395(6698): 194–8.

(39) Nikolic, M., H. Dudek, et al. (1996). "The cdk5/p35 kinase is essential for neurite outgrowth during neuronal differentiation." Genes & Development 10(7): 816–25.

(35) Ohshima, T., J. M. Ward, et al. (1996). "Targeted disruption of the cyclin-dependent kinase 5 gene results in abnormal corticogenesis, neuronal pathology and perinatal death." Proceedings of the National Academy of Sciences of the United States of America 93(20): 11173–8.

(41) Paglini, G., G. Pigino, et al. (1998). "Evidence for the participation of the neuron-specific cdk5 activator p35 during laminin-enhanced axonal growth." Journal of Neurscience 18:9858–69.

(48) Pant, A. C., Veeranna, et al. (1997). "Phosphorylation of human high molecular weight neurofilament protein (hNF-H) by neuronal cyclin-dependent kinase 5 (cdk5)." Brain Research 765(2): 259–66.

(34) Patrick, G. N., P. Zhou, et al. (1998). "p35, the neuronal-specific activator of cyclin-dependent kinase 5 (Cdk5) is degraded by the ubiquitin-proteasome pathway." Journal of Biological Chemistry 273(37): 24057–64.

(43) Paudel, H. K. (1997). "Phosphorylation by neuronal cdc2-like protein kinase promotes dimerization of Tau protein in vitro." Journal of Biological Chemistry 272 (45): 28328–34.

(42) Paudel, H. K., J. Lew, et al. (1993). "Brain proline-directed protein kinase phosphorylates tau on sites that are abnormally phosphorylated in tau associated with Alzheimer's paired helical filaments." Journal of Biological Chemistry 268(31): 23512–8.

(53) Pei, J. J., I. Grundke-lqbal, et al. (1998). "Accumulation of cyclin-dependent kinase 5 (cdk5) in neurons with early stages of Alzheimer's disease neurofibrillary degeneration." Brain Research 797(2): 267–77.

(12) Poorkaj, P., T. D. Bird, et al. (1998). "Tau is a candidate gene for chromosome 17 frontotemporal dementia." Annals of Neurology 43(6): 815–25.

(29) Qi, Z., Q. Q. Huang, et al. (1995). "Reconstitution of neuronal Cdc2-like kinase from bacteria-expressed Cdk5 and an active fragment of the brain-specific activator. Kinase activation in the absence of Cdk5 phosphorylation." Journal of Biological Chemistry 270(18): 10847–54.

Remington's Pharmaceutical Sciences, Mack Publishing Company, Easton, Pa., 16th ed., 1982.

Sambrook, J., E. F. Fritsch et al. "Molecular Cloning: A Laboratory Manual". 2nd ed., Cold Spring Harbor Press, New York, 1989.

(1) Selkoe, D. (1998) "The cell biology of beta-amyloid precursor protein and presenilin in Alzheimer's disease." Trends in Cell Biology 8: 447–53.

(50) Shuang, R., L. Zhang, et al. (1998). "Regulation of Munc-18/syntaxin 1A interaction by cyclin-dependent kinase 5 in nerve endings." Journal of Biological Chemistry 273(9): 4957–66.

(19) Sperber, B. R., S. Leight, et al. (1995). "Glycogen synthase kinase-3 beta phosphorylates tau protein at multiple sites in intact cells." Neuroscience Letters 197(2): 149–53.

(4) Spillantini, M. G. and M. Goedert (1998). "Tau protein pathology in neurodegenerative diseases." Trends in Neurosciences 21(10): 428–433.

(13) Spillantini, M. G., J. R. Murrell, et al. (1998). "Mutation in the tau gene in familial multiple system tauopathy with presenile dementia." Proceedings of the National Academy of Sciences of the United States of America 95(13): 773–741.

(47) Sun, D., C. L. Leung, et al. (1996). "Phosphorylation of the high molecular weight neurofilament protein (NF-H) by Cdk5 and p35." Journal of Biological Chemistry 271(24): 14245–51.

(33) Tang, D., A. C. S. Chun, et al. (1997). "Cyclin-dependent kinase 5 (Cdk5) activation domain of neuronal Cdk5 activator. Evidence of the existence of cyclin fold in neuronal Cdk5a activator." Journal of Biological Chemistry 272(19): 12318–27.

(25) Tang, D., K. Y. Lee, et al. (1996). "Neuronal Cdc2-like kinase: from cell cycle to neuronal function." Biochemistry & Cell Biology 74(4): 419–29.

(26) Tang, D. and J. H. Wang (1996). "Cyclin-dependent kinase 5 (Cdk5) and neuron-specific Cdk5 activators." Progress in Cell Cycle Research 2: 205–16.
(30) Tang, D., J. Yeung, et al. (1995). "An isoform of the neuronal cyclin-dependent kinase 5 (Cdk5) activator." Journal of Biological Chemistry 270(45): 26897–903.
(38) Tomizawa, K., H. Matsui, et al. (1996). "Localization and developmental changes in the neuron-specific cyclin-dependent kinase 5 activator (p35nck5a) in the rat brain." Neuroscience 74(2): 519–29.
(27) Tsai, L. H., I. Delalle, et al. (1994). "p35 is a neural-specific regulatory subunit of cyclin-dependent kinase 5." Nature 371(6496): 419–23.
(37) Tsai, L. H., T. Takahashi, et al. (1993). "Activity and expression pattern of cyclin-dependent kinase 5 in the embryonic mouse nervous system." Development 119(4): 1029–40.
(56) Wagner, T. E., P. C. Hoppe, et al. (1981). "Microinjection of a rabbit beta-globin gene into zygotes and its subsequent expression in adult mice and their offspring." Proceedings of the National Academy of Sciences of the United States of America 78(10): 6376–80.
(24) Wagner, U., J. Brownlees, et al. (1997). "Overexpression of the mouse dishevelled-1 protein inhibits GSK-3beta-mediated phosphorylation of tau in transfected mammalian cells." FEBS Letters 411(2–3): 369–72.
(21) Wagner, U., M. Utton, et al. (1996). "Cellular phosphorylation of tau by GSK-3 beta influences tau binding to microtubules and microtubule organisation." Journal of Cell Science 109(Pt 6): 1537–43.
(52) Yamaguchi, H., K. Ishiguro, et al. (1996). "Preferential labeling of Alzheimer neurofibrillary tangles with antisera for tau protein kinase (TPK) I/glycogen synthase kinase-3 beta and cyclin-dependent kinase 5, a component of TPK II." Acta Neuropathologica 92(3): 232–41.

What is claimed is:

1. A transgenic mouse and progeny thereof whose germ cells and somatic cell express recombinant DNA comprising a neuron specific enolase promoter operably linked to a p25 encoding sequence, wherein said mouse has increased brain total tau protein, increased brain tau phosphorylation, increased brain neurofilament H phosphorylation, or increased neutonal silver staining, as compared to a control mouse.

2. A method for determining the ability of a compound to inhibit a p25 polypeptide comprising the steps of:
   a. administering to the mouse of claim 1 the compound of interest; and
   b. measuring the inhibition of said p25 polypeptide by said compound.

3. A method for generating data to determine the ability of a compound to inhibit a p25 polypeptide comprising the steps of:
   a. administering to the mouse of claim 1 the compound of interest;
   b. measuring the inhibition of said p25 polypeptide by said compound; and
   c. using the data derived from said inhibition to synthesize compounds capable of inhibiting said p25 polypeptide.

* * * * *

SEQUENCE LISTING

<160> NUMBER OF SEQ ID NOS: 7

<210> SEQ ID NO 1
<211> LENGTH: 1867
<212> TYPE: DNA
<213> ORGANISM: Rattus rattus

<400> SEQUENCE: 1

```
ggatccccaa ttcgagctcc tcctctgctc gcccaatcct tccaaccccc tatggtggta      60
tggctgacac agaaaatgtc tgctcctgta tgggacattt gccctcttc tccaaatata       120 agacaggatg aggcctagct tttgctgctc caaagtttta aagaacaca ttgcacggca       180 tttagggact ctaaaggtg gaggaggaat gagggaattg catcatgcca aggctggtcc       240
tcatccatca ctgcttccag ggcccagagt ggcttccagg aggtattctt acaaaggaag      300
cccgatctgt agctaacact cagagcccat tttcctgcgt taaccccctcc cgacctcata    360 tacaggagta acatgatcag tgacctgggg gagctggcca aactgcggga cctgcccaag      420
ctgagggcct tggtgctgct ggacaacccc tgtgccgatg agactgacta ccgccaggag      480
gccctggtgc agatggcaca cctagagcgc ctagacaaag agtactatga ggacgaggac      540
cgggcagaag ctgaggagat ccgacagagg ctgaaggagg aacaggagca agaactcgac      600
ccggaccaag acatggaacc gtacctcccg ccaacttagt ggctcctcta gcctgcaggg      660
acagtaaagg tgatggcagg aaggcagccc ccggaggtca aaggctgggc acgcgggagg      720
agaggccaga gtcagaggct gcgggtatct cagatatgaa ggaaagatga gagaggctca      780
ggaagaggta agaaaagaca caagagacca gagaaggag aagaattaga gagggaggca     840
gaggaccgct gtctctacag acatagctgg tagagactgg gaggaaggga tgaaccctga    900
gcgcatgaag ggaaggaggt ggctggtggt atatggagga tgtagctggg ccagggaaaa      960
gatcctgcac taaaaatctg aagctaaaaa taacaggaca cggggtggag aggcgaaagg     1020
agggcagatt gaggcagaga gactgagagg cctggggatg tgggcattcc ggtagggcac     1080
acagttcact tgtcttctct ttttccagga ggccaaagat gctgacctca agaactcata     1140 atacccagt ggggaccacc gcattcatag ccctgttaca agaagtggga gatgttcctt      1200
tttgtcccag actggaaatc cattacatcc cgaggctcag gttctgtggt ggtcatctct     1260
gtgtggcttg ttctgtgggc ctacctaaag tcctaagcac agctctcaag cagatccgag     1320
gcgactaaga tgctagtagg ggttgtctgg agagaagagc cgaggaggtg ggctgtgatg     1380
```

```
gatcagttca gctttcaaat aaaaaggcgt ttttatattc tgtgtcgagt tcgtgaaccc    1440
ctgtggtggg cttctccatc tgtctgggtt agtacctgcc actatactgg aataagggga    1500
cgcctgcttc cctcgagttg gctggacaag gttatgagca tccgtgtact tatggggttg    1560
ccagcttggt cctggatcgc ccgggccctt cccccacccg ttcggttccc caccaccacc    1620
cgcgctcgta cgtgcgtctc cgcctgcagc tcttgactca tcggggcccc cgggtcacat    1680
gcgctcgctc ggctctatag gcgccgcccc ctgcccaccc ccgcccgcg ctgggagccg    1740 cagccgccgc cactcctgct ctctctgcgc cgccgccgtc accaccgcca ccgccaccgg    1800
ctgagtctgc agtcctcgac ctgcaggcat gcaagctggg taccgagctc gaattggtcg    1860
cggccgc                                                              1867

<210> SEQ ID NO 2
<211> LENGTH: 650
<212> TYPE: DNA
<213> ORGANISM: Homo sapiens

<400> SEQUENCE: 2
gcggccgcat ggcccagccc ccaccggccc agccgcctgc accccggcc agccagctct      60 cgggttccca gaccgggggc tcctcctcag tcaagaaagc ccctcaccct gccgtcacct    120
ccgcagggac gcccaaacgg gtcatcgtcc aggcgtccac cagtgagctg cttcgctgcc    180
tgggtgagtt tctctgccgc cggtgctacc gcctgaagca cctgtccccc acggaccccg    240
tgctctggct gcgcagcgtg accgctcgc tgcttctgca gggctggcag gaccagggct    300
tcatcacgcc ggccaacgtg gtcttcctct acatgctctg cagggatgtt atctcctccg    360
aggtgggctc ggatcacgag ctccaggccg tcctgctgac atgcctgtac ctctcctact    420
cctacatggg caacgagatc tcctacccgc tcaagccctt cctggtggag agctgcaagg    480
aggccttttg ggaccgttgc ctctctgtca tcaacctcat gagctcaaag atgctgcaga    540
taaatgccga cccacactac ttcacacagg tcttctccga cctgaagaac gagagcggcc    600
aggaggacaa gaagcggctc ctcctaggcc tggatcggtg aggcggccgc                650

<210> SEQ ID NO 3
<211> LENGTH: 717
<212> TYPE: DNA
<213> ORGANISM: Rous sarcoma virus

<400> SEQUENCE: 3
gcggccgcga ctctagagga tctttgtgaa ggaaccttac ttctgtggtg tgacataatt     60
ggacaaacta cctacagaga tttaaagctc taaggtaaat ataaaatttt taagtgtata    120
atgtgttaaa ctactgattc taattgtttg tgtattttag attccaacct atggaactga    180
tgaatgggag cagtggtgga atgcctttaa tgaggaaaac ctgttttgct cagaagaaat    240
gccatctagt gatgatgagg ctactgctga ctctcaacat tctactcctc caaaaaagaa    300
gagaaaggta gaagacccca aggactttcc ttcagaattg ctaagttttt tgagtcatgc    360
tgtgtttagt aatagaactc ttgcttgctt tgctatttac accacaaagg aaaaagctgc    420
actgctatac aagaaaatta tggaaaaata tttgatgtat agtgccttga ctagagatca    480
taatcagcca taccacattt gtagaggttt tacttgcttt aaaaaacctc ccacacctcc    540
ccctgaacct gaaacataaa atgaatgcaa ttgttgttgt taacttgttt attgcagctt    600
ataatggtta caaataaagc aatagcatca caaatttcac aaataaagca ttttttcac    660
```
tgcattctag ttgtggtttg tccaaactca tcaatgtatc ttatcatgtc tggatcc      717

<210> SEQ ID NO 4
<211> LENGTH: 3218
<212> TYPE: DNA
<213> ORGANISM: Multi organism source

<400> SEQUENCE: 4
ggatccccaa ttcgagctcc tcctctgctc gcccaatcct tccaacccc tatggtggta      60
tggctgacac agaaaatgtc tgctcctgta tgggacattt gccctcttc tccaaatata     120
agacaggatg aggcctagct tttgctgctc caaagtttta aagaacaca ttgcacggca     180
tttagggact ctaaagggtg gaggaggaat gagggaattg catcatgcca aggctggtcc     240
tcatccatca ctgcttccag ggcccagagt ggcttccagg aggtattctt acaaaggaag     300
cccgatctgt agctaacact cagagcccat tttcctgcgt taaccctcc cgacctcata     360
tacaggagta acatgatcag tgacctgggg gagctggcca aactgcggga cctgcccaag     420
ctgagggcct tggtgctgct ggacaacccc tgtgccgatg agactgacta ccgccaggag     480
gccctggtgc agatggcaca cctagagcgc ctagacaaag agtactatga ggacgaggac     540
cgggcagaag ctgaggagat ccgacagagg ctgaaggagg aacaggagca agaactcgac     600
ccggaccaag acatggaacc gtacctcccg ccaacttagt ggctcctcta gcctgcaggg     660
acagtaaagg tgatgcagg aaggcagccc ccggaggtca aggctgggc acgcgggagg      720
agaggccaga gtcagaggct gcgggtatct cagatatgaa ggaaagatga gagagctca     780
ggaagaggta agaaaagaca caagagacca gagaagggag aagaattaga gagggaggca     840
gaggaccgct gtctctacag acatagctgg tagagactgg gaggaaggga tgaaccctga     900
gcgcatgaag ggaaggaggt ggctggtggt atatggagga tgtagctggg ccagggaaaa     960
gatcctgcac taaaaatctg aagctaaaaa taacaggaca cggggtggag aggcgaaagg    1020
agggcagatt gaggcagaga gactgagagg cctggggatg tgggcattcc ggtagggcac    1080
acagttcact tgtcttctct ttttccagga ggccaaagat gctgacctca agaactcata    1140
atacccagt gggaccacc gcattcatag ccctgttaca agaagtggga gatgttcctt     1200
tttgtcccag actggaaatc cattacatcc cgaggctcag gttctgtggt ggtcatctct    1260
gtgtggcttg ttctgtgggc ctacctaaag tcctaagcac agctctcaag cagatccgag    1320
gcgactaaga tgctagtagg ggttgtctgg agagaagagc cgaggaggtg ggctgtgatg    1380
gatcagttca gctttcaaat aaaaggcgt ttttatattc tgtgtcgagt tcgtgaaccc      1440
ctgtggtggg cttctccatc tgtctgggtt agtacctgcc actatactgg aataagggga    1500
cgcctgcttc cctcgagttg gctggacaag gttatgagca tccgtgtact tatggggttg    1560
ccagcttggt cctggatcgc ccgggccctt ccccaccccg ttcggttccc caccaccacc    1620
cgcgctcgta cgtgcgtctc cgcctgcagc tcttgactca tcggggcccc cgggtcacat    1680
gcgctcgctc ggctctatag gcgccgcccc ctgcccaccc ccgcccgcg ctgggagccg     1740
cagccgccgc cactcctgct ctctctgcgc cgccgccgtc accaccgcca ccgccaccgg    1800
ctgagtctgc agtcctcgac ctgcaggcat gcaagctggg taccgagctc gaattggtcg    1860
cggccgcatg gcccagcccc caccggccca gccgcctgca ccccggcca gccagctctc     1920
gggttcccag accgggggct cctcctcagt caagaaagcc cctcaccctg ccgtcacctc    1980
cgcagggacg cccaaacggg tcatcgtcca ggcgtccacc agtgagctgc ttcgctgcct    2040
gggtgagttt ctctgccgcc ggtgctaccg cctgaagcac ctgtccccca cggaccccgt    2100

```
gctctggctg cgcagcgtgg accgctcgct gcttctgcag ggctggcagg accagggctt    2160
catcacgccg gccaacgtgg tcttcctcta catgctctgc agggatgtta tctcctccga    2220
ggtgggctcg gatcacgagc tccaggccgt cctgctgaca tgcctgtacc tctcctactc    2280
ctacatgggc aacgagatct cctacccgct caagcccttc ctggtggaga gctgcaagga    2340
ggccttttgg gaccgttgcc tctctgtcat caacctcatg agctcaaaga tgctgcagat    2400
aaatgccgac ccacactact tcacacaggt cttctccgac ctgaagaacg agagcggcca    2460
ggaggacaag aagcggctcc tcctaggcct ggatcggtga ggcggccgcg actctagagg    2520
atctttgtga aggaacctta cttctgtggt gtgacataat tggacaaact acctacagag    2580
atttaaagct ctaaggtaaa tataaaattt ttaagtgtat aatgtgttaa actactgatt    2640
ctaattgttt gtgtatttta gattccaacc tatggaactg atgaatggga gcagtggtgg    2700
aatgccttta atgaggaaaa cctgttttgc tcagaagaaa tgccatctag tgatgatgag    2760
gctactgctg actctcaaca ttctactcct ccaaaaaaga agagaaaggt agaagacccc    2820
aaggactttc cttcagaatt gctaagtttt ttgagtcatg ctgtgtttag taatagaact    2880
cttgcttgct ttgctatttta caccacaaag gaaaagctg cactgctata caagaaaatt    2940
atggaaaaat atttgatgta tagtgccttg actagagatc ataatcagcc ataccacatt    3000
tgtagaggtt ttacttgctt taaaaaacct cccacacctc ccctgaacc tgaaacataa    3060 aatgaatgca attgttgttg ttaacttgtt tattgcagct tataatggtt acaaataaag    3120
caatagcatc acaaatttca caaataaagc attttttca ctgcattcta gttgtggttt    3180
gtccaaactc atcaatgtat cttatcatgt ctggatcc                            3218

<210> SEQ ID NO 5
<211> LENGTH: 2462
<212> TYPE: DNA
<213> ORGANISM: Escherichia coli

<400> SEQUENCE: 5
gaactcgagc agctgaagct tgcatgcctg caggtcgact ctagaggatc cccgggtacc      60
gagctcgaat tcatcgatga tatcagatct gccggtctcc ctatagtgag tcgtattaat    120
ttcgataagc caggttaacc tgcattaatg aatcggccaa cgcgcgggga gaggcggttt    180
gcgtattggg cgctcttccg cttcctcgct cactgactcg ctgcgctcgg tcgttcggct    240
gcggcgagcg gtatcagctc actcaaaggc ggtaatacgg ttatccacag aatcagggga    300
taacgcagga agaacatgt gagcaaaagg ccagcaaaag ccaggaacc gtaaaaaggc    360 cgcgttgctg gcgtttttcc ataggctccg ccccctgac gagcatcaca aaaatcgacg    420
ctcaagtcag aggtggcgaa acccgacagg actataaaga taccaggcgt ttccccctgg    480
aagctccctc gtgcgctctc ctgttccgac cctgccgctt accggatacc tgtccgcctt    540
tctcccttcg ggaagcgtgg cgctttctca atgctcacgc tgtaggtatc tcagttcggt    600
gtaggtcgtt cgctccaagc tgggctgtgt gcacgaaccc cccgttcagc ccgaccgctg    660
cgccttatcc ggtaactatc gtcttgagtc aacccggta agacacgact tatcgccact    720
ggcagcagcc actggtaaca ggattagcag agcgaggtat gtaggcggtg ctacagagtt    780
cttgaagtgg tggcctaact acggctacac tagaaggaca gtatttggta tctgcgctct    840
gctgaagcca gttaccttcg gaaaaagagt tggtagctct tgatccggca acaaaccac    900 cgctggtagc ggtggttttt ttgtttgcaa gcagcagatt acgcgcagaa aaaaaggatc    960
```

-continued

```
tcaagaagat cctttgatct tttctacggg gtctgacgct cagtggaacg aaaactcacg    1020
ttaagggatt ttggtcatga gattatcaaa aaggatcttc acctagatcc ttttaaatta    1080
aaaatgaagt tttaaatcaa tctaaagtat atatgagtaa acttggtctg acagttacca    1140
atgcttaatc agtgaggcac ctatctcagc gatctgtcta tttcgttcat ccatagttgc    1200
ctgactcccc gtcgtgtaga taactacgat acgggagggc ttaccatctg gccccagtgc    1260
tgcaatgata ccgcgagacc cacgctcacc ggctccagat ttatcagcaa taaaccagcc    1320
agccggaagg gccgagcgca gaagtggtcc tgcaacttta tccgcctcca tccagtctat    1380
taattgttgc cgggaagcta gagtaagtag ttcgccagtt aatagtttgc gcaacgttgt    1440
tgccattgct acaggcatcg tggtgtcacg ctcgtcgttt ggtatggctt cattcagctc    1500
cggttcccaa cgatcaaggc gagttacatg atcccccatg ttgtgcaaaa aagcggttag    1560
ctccttcggt cctccgatcg ttgtcagaag taagttggcc gcagtgttat cactcatggt    1620
tatggcagca ctgcataatt ctcttactgt catgccatcc gtaagatgct tttctgtgac    1680
tggtgagtac tcaaccaagt cattctgaga atagtgtatg cggcgaccga gttgctcttg    1740
cccggcgtca atacgggata ataccgcgcc acatagcaga actttaaaag tgctcatcat    1800
tggaaaacgt tcttcgggc gaaaactctc aaggatctta ccgctgttga gatccagttc     1860
gatgtaaccc actcgtgcac ccaactgatc ttcagcatct tttactttca ccagcgtttc    1920
tgggtgagca aaaacaggaa ggcaaaatgc cgcaaaaaag ggaataaggg cgacacggaa    1980
atgttgaata ctcatactct tcctttttca atattattga agcatttatc agggttattg    2040
tctcatgagc ggatacatat ttgaatgtat ttagaaaaat aaacaaatag gggttccgcg    2100
cacatttccc cgaaaagtgc cacctgacgt ctaagaaacc attattatca tgacattaac    2160
ctataaaaat aggcgtatca cgaggccctt tcgtctcgcg cgtttcggtg atgacggtga    2220
aaacctctga cacatgcagc tcccggagac ggtcacagct tgtctgtaag cggatgccgg    2280
gagcagacaa gcccgtcagg gcgcgtcagc gggtgttggc gggtgtcggg gctggcttaa    2340
ctatgcggca tcagagcaga ttgtactgag agtgcaccat atggacatat tgtcgttaga    2400
acgcggctac aattaataca taaccttatg tatcatacac atacgattta ggtgacacta    2460
ta                                                                  2462
```

<210> SEQ ID NO 6
<211> LENGTH: 41
<212> TYPE: DNA
<213> ORGANISM: Homo sapiens

<400> SEQUENCE: 6

```
gcggccgcat ggcccagccc ccaccggccc agccgcctgc a                         41
```

<210> SEQ ID NO 7
<211> LENGTH: 34
<212> TYPE: DNA
<213> ORGANISM: Homo sapiens

<400> SEQUENCE: 7

```
ctcctcctag gcctggaatc ggtgaggcgg ccgc                                 34
```